United States Patent [19]

Sóti et al.

[11] Patent Number: 4,782,052

[45] Date of Patent: Nov. 1, 1988

[54] OCTAHYDROINDOLO[2,3-A]QUINOLIZIN-1-YL-ALKANECARBOXYLIC ACID AMINES AND THEIR THERAPEUTICALLY USEFUL ACID ADDITION SALTS, PHARMACEUTICAL COMPOSITIONS CONTAINING THEM AND PROCESS FOR PREPARING SAME

[75] Inventors: Ferenc Sóti; Csaba Szántay; Mária Incze; Zsuzsanna Balogh née Kardos; Elemér Ezer; Judit Matuz; László Szporny; György Hajós; Csaba Kuthi, all of Budapest, Hungary

[73] Assignee: Richter Gedeon Vegyeszeti Gyar Rt., Budapest, Hungary

[21] Appl. No.: 783,911

[22] Filed: Oct. 3, 1985

[30] Foreign Application Priority Data

Oct. 5, 1984 [HU] Hungary .................. 3776/84

[51] Int. Cl.$^4$ .................. A61K 31/55; A61K 31/535; C07D 471/04
[52] U.S. Cl. .................. 514/212; 514/253; 514/260; 514/275; 514/285; 514/233.2; 540/481; 540/597; 544/125; 544/284; 544/332; 544/361; 546/70
[58] Field of Search .................. 546/70; 514/285, 212, 514/234, 253, 260, 275; 540/481, 597; 544/125, 284, 332, 361

[56] References Cited

U.S. PATENT DOCUMENTS

4,117,133 9/1978 Bonati et al. .................. 514/280
4,353,911 10/1982 Buzas .................. 514/285

OTHER PUBLICATIONS

Balogh, et al., Chem. Abstracts, vol. 105, (1986), entry 60794h.

Primary Examiner—Donald G. Daus
Assistant Examiner—William A. Teoli, Jr.

Attorney, Agent, or Firm—Herbert Dubno; Jonathan Myers

[57] ABSTRACT

The invention relates to new 1,2,3,4,6,7,12,12b-octahydroindolo[2,3,-a]quinolizin-1-yl-alkanecarboxylic acid amides of the formula (I),

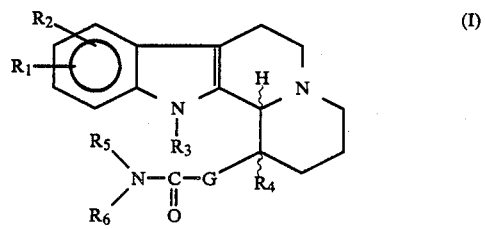

wherein
$R_1$ and $R_2$ stand independently for a hydrogen or halogen atom, or a hydroxyl, nitro or $C_{1-4}$ alkoxy group;
$R_3$ and $R_4$ stand independently for a hydrogen atom or a $C_{1-4}$ alkyl group;
$R_5$ and $R_6$ stand independently for a hydrogen atom, $C_{1-8}$ alkyl group, $C_{3-8}$ alkenyl or cycloalkyl group, aryl or aralkyl group, heteroaryl or heteroaralkyl group containing oxygen, nitrogen or sulphur atom, all these groups being optionally substituted; or
$R_5$ and $R_6$ together form an optionally substituted $C_{2-8}$ $\alpha,\omega$-alkylene group, wherein one carbon atom may optionally be replaced by an oxygen or nitrogen atom; and
G means a $C_{1-4}$ straight chained alkylene group, as well as to their therapeutically suitable acid addition salts and pharmaceutical compositions containing these compounds. The compounds of the formula (I) have valuable therapeutic properties, namely vasodilatory, spasmolytic, antiarrhythmic and gastrocytoprotective effects. The gastrocytoprotective effect is particularly important.

4 Claims, No Drawings

OCTAHYDROINDOLO[2,3-A]QUINOLIZIN-1-YL-ALKANECARBOXYLIC ACID AMINES AND THEIR THERAPEUTICALLY USEFUL ACID ADDITION SALTS, PHARMACEUTICAL COMPOSITIONS CONTAINING THEM AND PROCESS FOR PREPARING SAME

FIELD OF THE INVENTION

This invention relates to new 1,2,3,4,6,7,12,12b-octahydroindolo[2,3-a]quinolizin-1-yl-alkanecarboxylic acid amides of the formula (I),

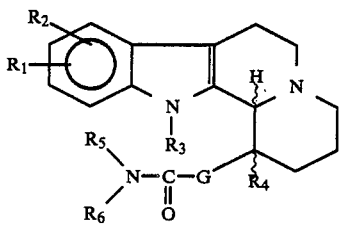

wherein $R_1$ and $R_2$ stand independently for a hydrogen or a halogen atom such as fluorine, chlorine or bromine atom, or a hydroxyl, nitro- or $C_{1-4}$ alkoxy group;

$R_3$ and $R_4$ stand independently for a hydrogen atom or a $C_{1-4}$ alkyl group;

$R_5$ and $R_6$ stand independently for a hydrogen atom, $C_{1-8}$ alkyl group, $C_{3-8}$ alkenyl or cycloalkyl group, aryl or aralkyl group, heteroaryl or heteroaralkyl group containing oxygen, nitrogen or sulphur atom, all these groups being optionally substituted; or $R_5$ and $R_6$ together form an optionally substituted $C_{2-8}$ α,ω-alkylene group, wherein one carbon atom may optionally be replaced by an oxygen or nitrogen atom; and G means a $C_{1-4}$ straight chain alkylene group, as well as to their therapeutically useful acid addition salts and pharmaceutical compositions containing these compounds.

According to another aspect of the invention, there is provided a process for the preparation of the new compounds of the formula (I), which comprises reacting an 1,2,3,4,6,7,12,12b-octahydroindolo[2,3-a]quinolizin-1-yl-alkanecarboxylic acid or a reactive derivative thereof of the formula (II),

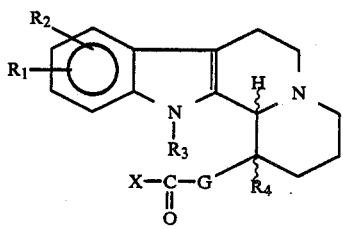

wherein

X stands for a hydroxyl group, an optionally substituted $C_{1-4}$ alkoxy group, an optionally substituted aryl-($C_{1-4}$)alkoxy group, an optionally substituted aryloxy group, a substituted aminoxy group, an aroyloxy, alkylcarbonyloxy, alkoxycarbonyloxy or an azido group or a halogen atom and $R_1$, $R_2$, $R_3$, $R_4$ and G are as defined above, with an amine of the formula (III),

wherein $R_5$ and $R_6$ are as defined above, and optionally transforming (converting) the thus-obtained compound of the formula (I) to a therapeutically useful acid addition salt.

BACKGROUND OF THE INVENTION

The 1,2,3,4,6,7,12,12b-octahydroindolo[2,3-a]-quinolizin-1-yl-alkanecarboxylic acid amide derivatives of the formula (I) according to the invention are new. There are some compounds known from the literature which are structurally related substances (Belgian patent specification No. 872,134; CA 91, 39454e; U.S. Pat. No. 4,353,911), wherein the substituted acid amide moiety is directly (i.e. without the interruption through an alkylidene chain) connected with the carbon atom in position 1 of the indolo[2,3-a]-quinolizine skeleton.

DESCRIPTION OF THE INVENTION

The compounds of the formula (I) are therapeutically active, they show a particularly valuable gastrocytoprotective action. Thus, the invention also relates to pharmaceutical compositions containing the compounds of the formula (I) or their therapeutically acceptable acid addition salts.

In the compounds of the formula (I) $R_3$ and $R_4$ as $C_{1-4}$ alkyl groups may stand for a straight or branched chained alkyl group, e.g. methyl, ethyl, n-propyl, isopropyl, n-butyl, isobutyl, secondary butyl or tertiary butyl group. As an unsubstituted $C_{2-8}$ α,ω-alkylene group, $R_5$ and $R_6$ together may represent e.g. an ethylene, trimethylene, tetramethylene, pentamethylene, hexamethylene, heptamethylene or octamethylene group; as a substituted $C_{2-8}$ α,ω-alkylene group, $R_5$ and $R_6$ may be the oxa- and aza-analogues of the preceding groups, such as the 3-oxa-pentamethylene or 3-methyl-3-aza-pentamethylene group; as $C_{1-8}$ alkyl groups $R_5$ and $R_6$ may stand for methyl, ethyl, n-propyl, n-butyl, n-pentyl, n-hexyl, n-heptyl or n-octyl group as well as their iso and/or branched chained analogues; as $C_{3-8}$ alkenyl groups $R_5$ and $R_6$ may stand for the unsaturated analogues of the above-mentioned alkyl groups such as an allyl group; as $C_{3-8}$ cycloalkyl groups $R_5$ and $R_6$ may be cyclopropyl, cyclobutyl, cyclopentyl, cyclohexyl, cycloheptyl or cyclooctyl group; as aryl or heteroaryl groups, respectively, $R_5$ and $R_6$ may represent phenyl, pyridyl, furyl, tienyl or pyrrolyl group or their analogues containing more heteroatoms and/or one or more condensed rings such as an imidazolyl, pyrimidinyl, thiazolyl, naphthyl quinolinyl, indolyl or quinolizinyl group; as aralkyl or heteroaralkyl groups, respectively, $R_5$ and $R_6$ may stand for an aryl-($C_{1-6}$)alkyl group such as benzyl, 1-phenylethyl, 2-phenylethyl, 4-phenylbutyl, furfuryl, 2-pyridylmethyl, thiophen-2-ylmethyl or 2-(3-indolyl)-ethyl group; when substituted, $R_5$ and $R_6$ may contain one or more identical or different substituents such as halogen, e.g. fluorine, chlorine or bromine atom, or hydroxyl, $C_{1-4}$ alkyl, $C_{1-4}$ alkoxy, aryl, halogenated alkyl or acyl group. As a straight chained $C_{1-4}$ alkylene group G may stand for a methylene, ethylene, ethylidene or propylidene group.

As a $C_{1-4}$ alkoxy or alkenyloxy group X in the formula (II) of the compounds, used as starting materials in the process of the invention, may represent a methoxy, ethoxy or vinyloxy group; as a substituted $C_{1-4}$ alkoxy group X may stand for a cyanomethoxy group; as an aryloxy group X may stand e.g. for a phenoxy or pyridyloxy group; as a substituted aryloxy group X may represent e.g. a nitrophenoxy or pentachlorophenoxy group; as a substituted aminoxy group X may represent e.g. a succinimidoxy or benzotriazolyloxy group; as an aroyloxy group X may stand e.g. for a benzoyloxy group; as an alkylcarbonyloxy group X may represent e.g. an isovaleryloxy or pivaloyloxy group; as an alkyloxycarbonyl group X may mean e.g. an ethoxycarbonyloxy, isobutoxycarbonyloxy, tertiary butoxycarbonyloxy or benzyloxycarbonyloxy group.

In the amines of the formula (III), used as starting materials in the process of the invention, $R_5$ and $R_6$ may mean the same as defined above in detail.

The 1,2,3,4,6,7,12,12b-octahydroindolo[2,3-a]quinolizin-1-yl-alkanecarboxylic acid amide derivatives of the formula (I) and their acid addition salts are new compounds and possess valuable therapeutic actions, e.g. spasmolytic, vasodilatory, antiarrhythmic and gastrocytoprotective effect. Their gastrocytoprotective effect is particularly important.

The gastrocytoprotective action of the compounds of the invention was investigated by using the test methods given below. The results are summarized in Tables containing the data obtained with RGH-2961, a particularly effective compound of the invention which is chemically (—)-(1S,12bS)-1-ethyl-1,2,3,4,6,7,12,12b-octahydroindolo[2,3-a]quinolizin-1-yl-propionic acid (R)-1-phenylethylamide.

Inhibition of the gastric acid secretion in Shay rats (Gastroenterology 5, 43 /1945/)

Female H-Wistar rats weighing 120 to 150 g were starved for 24 hours while receiving water ad libitum. Then, the pylorus of the animals was ligated under a mild ether anesthesia. The test substances were administered orally or intraperitoneally. After 4 hours the animals were killed by an overdose of ether and after excision of the stomach, the volume and pH value of the gastric juice were measured. The acid content was determined by titration against 0.01N sodium hydroxide solution by using phenolphthalein as indicator. The results of these investigations are summarized in Table 1.

TABLE 1

| Inhibition of gastric acid secretion in Shay rats (oral and intraperitoneal treatments) | | | | |
|---|---|---|---|---|
| Treatment | N | Dose mg./kg. | HCl output (4 hours μmole/100 g. of body weight ± S.E.M. | HCl output inhibition % |
| Control | 10 | — | 520 ± 28 | — |
| RGH-2961 | 5 | 10 p.o. | 483 ± 40 | 8 |
| RGH-2961 | 5 | 20 p.o. | 468 ± 35 | 10 |
| RGH-2961 | 5 | 40 p.o. | 409 ± 30 | 22 |
| RGH-2961 | 5 | 6 i.p. | 425 ± 40 | 19 |
| RGH-2961 | 5 | 12 i.p. | 195 ± 25 | 63[x] |

TABLE 1-continued

| Inhibition of gastric acid secretion in Shay rats (oral and intraperitoneal treatments) | | | | |
|---|---|---|---|---|
| Treatment | N | Dose mg./kg. | HCl output (4 hours μmole/100 g. of body weight ± S.E.M. | HCl output inhibition % |
| RGH-2961 | 5 | 25 i.p. | 0 | 100 |

[x]p < 0.01 as compared to the control group

Inhibition of the aspirin-induced stomach ulcer in rats

This test is very common in the pharmacological practice. Female H-Wistar rats weighing 120 to 150 g. were starved for 24 hours while receiving water ad libitum. The stomach ulcer was induced by the oral administration of 100 mg./kg. aspirin in a Tween 80 suspension. The test substance was given immediately after the aspirin treatment. At the end of the 4th hour after treatment the animals were killed by an overdose of ether, their stomach was excised and cut along the major curvature. The stomach content was washed out and the hemorrhagic lesions on the glandular surface were counted. The results are summarized in Table 2.

TABLE 2

| The dose-dependent inhibiting effect of RGH-2961 on the aspirin-induced gastric ulcer formation in rats (the substances were given simultaneously) | | | | |
|---|---|---|---|---|
| Treatment | N | Dose mg./kg. p.o. | No. of ulcers per stomach ± S.E.M. | Inhibition % |
| Aspirin control | 20 | 100 | 16.6 ± 5 | — |
| RGH-2961 + aspirin | 10 | 5 | 7.1 ± 2 | 58[x] |
| RGH-2961 + aspirin | 10 | 10 | 11.0 ± 3 | 32 |
| RGH-2961 + aspirin | 20 | 20 | 3.5 ± 2.1 | 79[x] |
| RGH-2961 + aspirin | 10 | 50 | 2.5 ± 1.5 | 85[x] |

[x]p < 0.01 as compared to the aspirin control group
The oral $ED_{50}$ is 8.0 mg.kg.

Inhibition of the ethanolic hydrochloric acid-induced gastric necrosis

Female RG-Wistar rats weighing 120 to 150 g. were used for these investigations. The animals were starved for 24 hours while receiving water ad libitum. Acid-containing ethanol (which had been prepared by dissolving 1 ml. of 36% hydrochloric acid in 50 ml. of ethanol) was used as necrotizing agent given in an oral dose of 0.5 ml ml./100 g. of body weight. The test substances were orally administered 30 minutes before the treatment with the ethanolic hydrochloric acid. One hour later the animals were killed by an overdose of ether. Their stomach was removed and cut along the major curvature. The stomach was cleaned and its wet weight was weighed. The gastric edema was calculated from the difference between the obtained wet weight and the wet weight of the stomach of the untreated animals. Thereafter, the stomach was dried at room temperature and the presence of the hemorrhagic lesions was visually observed on the next day. The degree of the gastric necrosis was characterized by the mean value of the damage in mm./stomach. The results were statistically evaluated by Student's test. The results are summarized in Table 3.

TABLE 3

The dose-dependent prevention by RGH-2961 of the ethanolic hydrochloric acid induced gastric edema and hemorrhagic lesions in rats

| Pretreatment | N | Dose mg./kg. | Edema mg. ± S.E.M. | Inhibition % | Hemorrhagic lesions mm. ± S.E.M. | Inhibition % |
|---|---|---|---|---|---|---|
| Ethanolic hydrochloric acid control | 7 | — | 349 ± 81 | — | 132 ± 7 | — |
| RGH-2961 | 7 | 1 | 345 ± 93 | 0 | 88 ± 28 | 36 |
| RGH-2961 | 7 | 10 | 197 ± 52 | 44 | 51 ± 9 | $62^x$ |
| RGH-2961 | 7 | 50 | 53 ± 41 | $85^x$ | 17 ± 6 | $88^x$ |
| Cimetidine* | 8 | 100 | 301 ± 42 | 14 | 42 ± 13 | $69^x$ |

$^x$p < 0.01 as compared to the ethanolic hydrochloric acid control group
The oral $ED_{50}$ value of the gastric edema inhibition is 12.5 mg./kg.
The oral $ED_{50}$ value of the gastric hemorrhagic lesion inhibition is 3.0 mg./kg.
*Reference drug

Inhibition of the Indomethacin-induced intestinal ulceration

Unstarved H-Wistar rats weighing 120 to 150 g. were used for these investigations. The animals were orally treated with Indomethacin. Under these conditions a period of 24 to 48 hours is at least required for the development of visually observable intestinal ulcers.

For evaluating the small intestine ulcers, the tensile strength of the intestinal wall was determined by using the inflation method of Ezer and Sporny (1975), as the strength of the intestinal wall is diminished by the ulceration-induced erosion.

The small intestine from the pylorus down to the caecum was removed and after ligation of the end it was connected through a polyethylene tube with a W+W electronic BP 8005 pressure recorder (Ugo Basile, Italy). The whole small intestine was placed into a 0.9% saline solution at 37° C. and the pressure was increased until air bubbles appeared at the attenuated (weakened) sites of the intestinal wall. This pressure as expressed in mmHg is the measure of the tensile strength. The results of this study are summarized in Table 4.

through the oesophagus. For removing all solid contents, the stomach was flushed with a 0.9% saline solution, taking care to avoid any distension. Two hours after the surgery, the stomach was again washed out with a 4-ml. aliquot of saline solution in order to remove the acid secreted as a consequence of the surgical intervention. One hour after this washing-out, histamine was subcutaneously injected in a dose of 3 mg./kg. of body weight. After this administration the stomach was flushed in every 30 minutes. The solution obtained was titrated against 0.01N sodium hydroxide solution by using phenyolphthalein as indicator, or determined by using a Radelkis-OP-213 acid-base meter. The acid output was expressed as microequivalent ($\mu$Eq) of hydrochloric acid per 30 minutes.

It is obvious from the results that the compounds of the invention are active in rats by showing:

a prevention of the development of gastric necrosis, i.e. gastric edema and hemorrhages induced by ethanolic hydrochloric acid;

an inhibition of the aspirin-induced gastric ulceration; and a prophylactic effect against the indomethacin-

TABLE 4

The dose-dependent prophylactic effect of RGH-2961 on the Indomethacin-induced ulceration in rats

| Simultaneous treatments on 3 consecutive days | N | Dose mg./kg. p.o. | Tensile strength of the intestinal wall at 24 hours after the last treatment mmHg ± S.E.M. | Resistance of the intestinal wall as % of the normal value |
|---|---|---|---|---|
| Untreated | 50 | — | 237 ± 4 | 100 |
| Indomethacin-control | 30 | 3 × (veh. + 10) | 72 ± 10 | 30 |
| RGH-2961 + Indomethacin | 10 | 3 × (12 + 10) | 132 ± 16 | 55 |
| RGH-2961 + Indomethacin | 10 | 3 × (25 + 10) | 195 ± $8^x$ | 82 |
| RGH-2961 + Indomethacin | 10 | 3 × (50 + 10) | 214 ± $6^x$ | 90 |
| Pirenzepine + Indomethacin* | 10 | 3 × (50 + 10) | 121 ± 26 | 51 |
| Cimetidine + Indomethacine* | 10 | 3 × (50 + 10) | 20 ± $25^x$ | 8 |

$^x$p 0.001 as compared to the Indomethacin control group
*Reference drug

Inhibition of the histamine-stimulated gastric acid secretion in the perfused rat stomach The perfusion was carried out by using the method of Ghosh and Schild (Brit. J. Pharmacol. 13, 54 /1958/) with some modifications.

Male rats weighing 300 to 350 g. were starved for 24 hours while receiving water ad libitum. Anesthesia was induced by administering a 10% solution of urethane (1 ml./100 g. of body weight i.p.). The abdomen was opened by a transverse incision and a glass cannula was introduced to the stomach through an incision made on the duodenum. A polyethylene cannula was led induced intestinal ulceration.

The effective doses are lower than those required for the inhibition of the acid secretion in Shay rats. In the perfused rat stomach, the histamine- or carbachol-induced acid secretion was not inhibited by the compounds of the invention; thus, the mechanism of this inhibiting effect is believed to be new.

The toxicity of the compounds of the invention is low: the oral value of the particularly effective compound RGH-2961, chemically (−)-(1S,12bS)-1-ethyl-1,2,3,4,6,7,12,12b-octahydroindolo[2,3-a]quinolizin-1-yl-propionic acid (R)-1-phenylethylamide, is higher than 1500 mg./kg. in rats.

The 1,2,3,4,6,7,12,12b-octahydroindolo[2,3-a]quinolizin-1-yl-alkanecarboxylic acids of the formula (II), wherein X stands for a hydroxyl group, used as a starting materials in the process of the invention, may be prepared according to the literature (L. Szabó et al: Archiv der Pharmazie 316, 629 (1983); M. E. Kuehne: J. Am. Chem. Soc. 86, 2946/1964/; and M. F. Bartlett and W. I. Taylor: J. Am. Chem. Soc. 82, 5941/1960/).

The amines of the formula (III) are known in the literature (Beilsteins Handbuch der Organischen Chemie 4, 12; Houben-Weyl: Methoden der Organischen Chemie Vol. 11, Part 1) and most of them are commercially available.

According to the process of the invention, the compounds of the formula (I) are synthesized by the formation of the amide group. A number of methods are known in the literature for the formation of the amide group (e.g. M. Bodánszky et al.: Peptide Synthesis, page 85, John Wiley and Sons, New York 1976; Houben-Weyl: Methoden der Organischen Chemie, Vol. 15, Part 2, page 1, Georg Thieme Verlag, Stuttgart, 1974).

For the preparation of the new compounds of the formula (I), an amine of the formula (III) may be acylated with an alkanecarboxylic acid of the formula (II), wherein X means a hydroxyl group and $R_1$, $R_2$, $R_3$, $R_4$ and G are as defined above; however, the acylation may be carried out by using an alkanecarboxylic acid derivative of the formula (II), wherein X is as defined above but different from the hydroxyl group and $R_1$, $R_2$, $R_3$, $R_4$ and G are as defined above.

On acylating with an alkanecarboxylic acid of the formula (II), wherein X stands for hydroxyl group, the acid of the formula (II) is reacted with an amine of the formula (III) at room temperature in an inert organic solvent in the presence of an appropriate condensing agent. Suitable solvents are e.g. tetrahydrofuran, dioxane, acetonitrile or dichloromethane. A preferred condensing agent is N,N'-dicyclohexylcarbodiimide, but dichloromethyl methyl ether, ethoxyacetylene, diphenylketene, diphenylphosphoryl azide or a mixture of triphenyl phosphite with imidazole may also be used. A catalyst can also be used in order to increase the yield of this reaction. Suitable catalysts are e.g. N-hydroxysuccinimide or 1-hydroxybenzotriazole. When the boiling point of the amine of the formula (III) is high enough, e.g. in the case of 1-phenylethylamine, 4-phenylbutylamine, diethanolamine or dibenzylamine, then the acylation with an alkanecarboxylic acid of the formula (II) may be achieved directly by boiling the components in xylene or chlorobenzene while removing the water formed from the system in the form of an azeotropic mixture. The methyl or ethyl ester of the alkanecarboxylic acid of the formula (II) may also be used for acylation in such a way that the components are heated as a melt. This melting process may be carried out with the components alone or in the presence of a suitable catalyst such as an alkaline metal alkoxide or 2-hydroxypyridine by distilling out the formed methanol or ethanol from the system.

A more preferred and generally suitable method for preparing the new alkanecarboxylic acid amides of the formula (I) consists in that an amine of the formula (III) is acylated with a reactive alkanecarboxylic acid derivative of the formula (II), wherein X is as defined above but different from the hydroxyl group. In this case the alkanecarboxylic acid of the formula (II) is transformed to an ester, mixed anhydride, acid chloride or acyl azide, preferably to a mixed anhydride in a manner known in the art. These reactive acid derivatives are prepared in situ and used without isolation from the acylation of the amine of the formula (III). Obviously, the reactive alkanecarboxylic acid derivatives may be isolated, if desired.

For forming the amide linkage, the mixed anhydrides may be prepared as described in the above-cited literature references. Suitable mixed anhydrides can be formed e.g. by using pivaloyl chloride or chloroformate esters, e.g. with ethyl, isobutyl, tertiary butyl or benzyl chloroformate, preferably with ethyl chloroformate. It is suitable to use an acid binding agent in this various reaction, e.g. an organic base which cannot be acylated such as triethylamine, tributylamine, dimethyl- or diethylaniline, N-ethyldiisopropylamine, N-methylmorpholine, N-ethylpiperidine or a mixture thereof. The preferred acid binding agent is N-methylmorpholine.

Suitable solvents for this reaction are inert organic solvents such as aromatic hydrocarbons, e.g. benzene, toluene; chlorinated hydrocarbons, e.g. chloroform, dichloromethane or chlorobenzene; ethers, e.g. diethyl ether or diisopropyl ether; cyclic ethers, e.g. dioxane or tetrahydrofuran; esters, e.g. ethyl acetate; and other aprotic organic solvents, e.g. acetone, acetonitrile or their mixture. A preferred solvent is tetrahydrofuran.

The mixed anhydride may be prepared at a temperature between $-25°$ C. and $+5°$ C., preferably between $0°$ C. and $-5°$ C. The mixed anhydride is reacted with the amine of the formula (III) at a temperature between $-25°$ C. and $+5°$ C., preferably between $0°$ C. and $-5°$ C., then the reaction is completed by stirring for additional 3 to 4 hours at room temperature. The alkanecarboxylic acid amides of the formula (I) may be obtained e.g. in such a way that the reaction mixture is evaporated and the residue is mixed with a water-immiscible organic solvent, such as aromatic hydrocarbons, e.g. toluene or benzene; or with a chlorinated hydrocarbon, e.g. chloroform or dichloromethane; or with another water-immiscible solvent, e.g. ethyl acetate; preferably with dichloromethane and water, whereupon the organic phase is separated and extracted with a mildly alkaline aqueous solution, suitably with a 5% sodium carbonate solution and water, then dried and evaporated. The evaporation residue is a crude product which may be purified by chromatography, preferably on a column prepared with silica gel by using toluene containing diethylamine as eluant. Recrystallization of the crude product may also be employed for purification.

If desired, the compounds of the formula (I) prepared by using the process of the invention may be transformed to acid addition salts. These salts may be formed in such a way that the compound of the formula (I) is dissolved e.g. in a $C_{1-6}$ aliphatic alcohol and an appropriate acid or a solution of this acid in the above solvent is portionwise added until the pH value of the mixture becomes acidic. The acid addition salt precipitated from the mixture is separated in a suitable manner, e.g. by filtration.

The active compounds of the formula (I) can be converted into pharmaceutical compositions by mixing them with the usual non-toxic inert solid or liquid carriers and/or auxiliary agents which are commonly used in compositions suitable for enteral or parenteral administration. As carriers e.g. water, gelatine, lactose, starch, pectin, magnesium stearate, stearic acid, talc and vegetable oils such as peanut oil or olive oil or the like can be employed. The active ingredient can be formulated to the usual pharmaceutical compositions, particularly to solid forms such as rounded or angled tablets, dragées, capsules, e.g. gelatine capsules, pills, suppositories or the like. The amount of the solid carrier materials can vary between wide limits, preferably they are used in an amount between about 25 mg. and 1 g. The compositions may optionally contain the commonly used pharmaceutical additives, e.g. preserving agents, stabilizers, wetting agents and emulsifying agents or the like.

The pharmaceutical compositions are prepared by using the common methods involving e.g. sieving, mixing, granulating and pressing. The compositions may be subjected to further operations (e.g. sterilization) commonly used in the pharmaceutical industry.

SPECIFIC EXAMPLES

The invention is illustrated in detail by the aid of the following non-limiting Examples.

Example 1

Preparation of
(−)-(1S,12bS)-1-ethyl-1,2,3,4,6,7,12,12b-octahydroindolo[2,3-a]quinolizin-1-yl-propionic acid benzylamide 3.26 g. (0.01 mole) of (−)-(1S,12bS)-1-ethyl-1,2,3,4,6,7,12,12b-octahydroindolo[2,3-a]quinolizin-1-yl-propionic acid are added to a solution containing 2.04 g. (0.02 moles) of N-methylmorpholine (redestilled from sodium) in 20 ml. of dry tetrahydrofuran while stirring under nitrogen, then the solution is cooled to −5° C. and 1.10 g. (0.01 mole) of ethyl chloroformate are rapidly dropped in while stirring vigorously and keeping the inner temperature at or lower than 0° C. The mixture is stirred at 0° C. for 30 minutes, then a mixture containing 1.18 g. (0.011 moles) of benzylamine in 10 ml. of dry tetrahydrofuran is dropwise added during 10 minutes at a temperature between −5° C. and 0° C. Then the mixture is stirred at 0° C. for 30 minutes and during an additional stirring for 4 hours the temperature of the mixture is allowed to warm to room temperature. The mixture is evaporated on a rotating evaporator. After shaking thoroughly the evaporation residue with 50 ml of dichloromethane and 20 ml of water, the organic layer is separated, washed successively with 20 ml. of 5% sodium carbonate solution, then 3 times with 20 ml of water each, dried on magnesium sulphate and evaporated. The crude product obtained as distillation residue is purified by column chromatography on silica gel by using toluene containing 10% of diethylamine as eluating agent.

The title product (aimed product) is obtained in a yield of 2.35 g. (57%) and can further be purified by recrystallization from toluene, m.p.: 95°–99° C., $[\alpha]_D^{25} = -128.8°$ (c=2.0, chloroform).

Analysis: calculated for $C_{27}H_{33}N_3O$ (molecular weight 415.56): C 78.03; H 8.00; N 10.11%. found: C 77.90; H 8.49; N 9.68%.

$^1$H-NMR spectrum (CDCl$_3$): δ1.10 (3H, t, J=7 Hz, Cl—CH$_2$—CH$_3$), 3.35 (1H, C12b—H), 4.30 (2H, d, $J_{CH_2,NH}=6$ Hz, pH—CH$_2$), 5.53 (1H, broad t, CO—NH), 7.0–7.47 (9H, m, aromatic protons), 7.96 (1H, broad s, indole NH) ppm.

The *ethanesulphonate salt* melts at 169°–171° C. (after recrystallization from a mixture of isopropanol and ethyl acetate), $[\alpha]_D^{27} = -74.1°$ (c=2.0, water).

Analysis: calculated for $C_{29}H_{39}N_3O_4S$ (moleculare weight 525.69): C 66.25; H 7.48; N 7.99; óS 6.10%. found: C 66.39; H 6.99; N 7.91; s 6.69%.

Example 2

Preparation of
(−)-(1S,12bS)-1-ethyl-1,2,3,4,6,7,12,12b-octahydroindolo[2,3-a]quinolizin-1-yl-propionic acid
(S)-1-phenylethylamide Starting from 1.33 g. (0.011 moles) of (S)-1-phenylethylamine as amine component, the process described in Example 1 is used and the crude product is purified by column chromatography on silica gel by using toluene containing 5% of diethylamine as eluant. Thus, the aimed (title) compound is obtained as a foamy product in a yield of 2.57 g. (60%).

$^1$H-NMR spectrum (CDCl$_3$): δ1.07 (3H, t, J=7 Hz, Cl—CH$_2$CH$_3$), 1.32 (3H, d, $J_{CH,CH_3}=7$ Hz, NH—CH—CH$_3$), 3.33 (1H, C12b—H), 4.99 (1H, m, NH—CH—CH$_3$), 5.40 (1H, broad d, $J_{NH,CH}=7$ Hz, CO—NH), 7.0–7.49 (9H, m, aromatic protons), 8.02 (1H, broad s, NH) ppm.

The *phosphate salt* melts at 160°–168° C. (after recrystallization from isopropanol), $[\alpha]_D^{25} = -98.2°$ (c=2.0, water).

The *hydrobromide salt* melts at 172°–175° C. (after recrystallization from isopropanol).

The *hydrochloride salt* melts at 170°–176° C. (after recrystallization from isopropanol).

Example 3

Preparation of
(−)-(1S,12bS)-1-ethyl-1,2,3,4,6,7,12,12b-octahydroindolo[2,3-a]quinolizin-1-yl-propionic acid
(R)-1-phenylethylamide Starting from 1.33 g (0.011 moles) of (R)-phenylethylamine as amine component, the process described in Example 1 is used and the crude product is purified by recrystallization from isopropanol to give the aimed (title) compound in a yield of 2.92 g. (68%), m.p.: 154°–156° C., $[\alpha]_D^{30} = -50.4°$ (c=2.0, ethanol).

Analysis: calculated for $C_{28}H_{35}N_3O$ (molecular weight 429.58): C 78.28; H 8.21; N 9.78%. found: C 78.05; H 8.40; N 9.77%.

$^1$H-NMR spectrum (CDCl$_3$): δ1.05 (3H, t, J=7 Hz, Cl—CH$_2$—CH$_3$), 1.37 (3H, d, $J_{CH,CH_3}=7$ Hz, NH—CH—CH$_3$), 3.33 (1H, C12b—H), 5.00 (1H, m, NH—CH—CH$_3$), 5.40 (1H, broad d, $J_{NH,CH}=7$ Hz, CO—NH), 7.0–7.50 (9H, m, aromatic protons), 8.0 (1H, broad s, indole NH) ppm.

The *phosphate salt* melts at 198°–204° C. (after recrystallization from isopropanol), $[\alpha]_D^{25} = -32.4°$ (c=1.0, water).

The *hydrobromide salt* melts at 185°–192° C. (after recrystallization from isopropanol).

The *ethanesulphonate salt* melts at 143°–150° C. (after recrystallization from the mixture of isopropanol and diisopropyl ether).

The *methanesulphonate salt* melts at 155°–165° C. (after recrystallization from the mixture of isopropanol and diisopropyl ether).

The hydrochlorid salt melts at 195°–200° C. (after recrystallization from isopropanol), $[\alpha]_D^{30} = -2.6°$ (c=2.0, ethanol).

Analysis: calculated for $C_{28}H_{36}ClN_3O$ (molecular weight 466.04): C 72.16; H 7.79; N 9.02; Cl (ionic) 7.61%. found: C 72.01; H 7.57; N 8.87; Cl (ionic) 7.53%.

Example 4

Preparation of (−)-(1S,12bS)-1-ethyl-1,2,3,4,6,7,12,12b-octahydroindolo[2,3-a]quinolizin-1-yl-propionic acid n-hexylamide Starting from 1.10 g. (0.011 moles) of n-hexylamine as amine component, the process described in Example 1 is followed and the crude product is purified by column chromatography on silica gel by using toluene containing 5% of diethylamine as eluant to give 1.88 g (46% yield) of the title compound in the form of a foamy product.

$^1$H-NMR spectrum (CDCl$_3$): δ1.08 (3H, t, J=7 Hz, Cl—CH$_2$—CH$_3$), 0.84 (3H, t, J=6 Hz, NH—(CH$_2$)$_5$—CH$_3$), 3.34 (1H, C12b—H), 5.20 (1H, broad t, CO—NH), 7.0–7.50 (4H, m, aromatic protons), 8.06 (1H, broad s, indole NH) ppm.

The *ethanesulphonate salt* melts at 147°–150° C. (after recrystallization from the mixture of isopropanol and diisopropyl ether), [α]$_D^{25}$= −63.4° (c=2.0, water).

Analysis: calculated for C$_{28}$H$_{45}$N$_3$O$_4$S (molecular weight 519.73): C 64.70; H 8.72; N 8.09; S 6.17%. found: C 64.39; H 8.51; N 7.76; S 6.35%.

Example 5

Preparation of (−)-(1S,12bs)-1-ethyl-1,2,3,4,6,7,12,12b-octahydroindolo[2,3-a]quinolizin-1yl-propionic acid N-methylbenzylamide Starting from 1.34 g (0.011 moles) of N-methylbenzylamine as amine component, the process described in Example 1 is followed. The crude product is purified by column chromatography on silica gel by using toluene containing 5% of diethylamine as eluant to give 2.40 g. (56% yield) of the title compound in the form of a foamy product.

$^1$H-NMR spectrum (CDCl$_3$): δ1.18 (3H, t, J=7 Hz, ClCH$_2$—CH$_3$), 2.01 (3H, s, N—CH$_3$), 3.32 (1H, C12b—H), 4.32 (2H, broad, Ph—CH$_2$), 6.9–7.4 (4H, m, aromatic protons), 7.96 (1H, broad s, indole NH) ppm.

The ethanesulphonate salt melts at 200°–207° C. (after recrystallization from a mixture of isopropanol and diisopropyl ether), [α]$_D^{25}$= −84.2° (c=2.0, water).

Analysis: calculated for C$_{30}$H$_{41}$N$_3$O$_4$S (molecular weight 539.71): C 66.76; H 7.66; N 7.79; S 5.94%. found: C 66.11; H 7.96; N 7.32; S 6.21%.

The *hydrobromide salt* melts at 200°–220° C. (after recrystallization from acetone).

The *hydrochloride salt* melts at 175°–197° C. (after recrystallization from acetone).

Example 6

Preparation of (−)-(1S,12bS)-1-ethyl-1,2,3,4,6,7,12,12b-octahydroindolo[2,3-a]quinolizin-1-yl-propionic acid furfurylamide Starting from 1.08 g. (0.011 moles) of furfurylamine as amine component, the process described in Example 1 is followed. The crude product is purified by column chromatography on silica gel by using toluene containing 5% of diethylamine as eluant to give 2.18 g. (54% yield) of the title compound in the form of a foamy product.

$^1$-NMR spectrum (CDCl$_3$): δ1.08 (3H, t, J=7 Hz, Cl—CH$_2$—CH$_3$), 3.33 (1H, C12b—H), 4.27 (2H, d, J$_{CH_2,NH}$=5 Hz, NH—CH$_2$), 5.34 (1H, broad t, CO—NH), 6.10 (1H, m, J$_{3',4'}$=1 Hz, C3'—H), 6.26 (1H, m, J$_{3',4'}$=3 Hz, J$_{4',5'}$=2 Hz, C4'—H), 7.0–7.47 (5H, m, aromatic protons+C5'—H), ppm.

The *ethanesulphonate salt* melts at 142°–146° C. (after recrystallization from the mixture of isopropanol and diisopropyl ether), [α]$_D^{25}$= −65.9° (c=2.0, water).

Analysis: calculated for C$_{27}$H$_{37}$N$_3$O$_5$S (molecular weight 515.65): C 62.89; H 7.23; N 8.15%. found: C 63.40; H 7.35; N 7.93%;

Example 7

Preparation of (−)-(1S,12bS),1-ethyl-1,2,3,4,6,7,12,12b-octahydroindolo[2,3-a]quinolizin-1-yl-propionic acid 2-(3,4-dimethoxyphenyl)-ethylamide Starting from 2.00 g. (0.011 moles) of 2-(3,4-dimethoxyphenyl)-ethylamine as amine component, the process described in Example 1 is followed. The crude product is purified by column chromatography on silica gel by using toluene containing 5% of diethylamine as eluant to give 2.64 g. (54% yields) of the title compound in the form of a foamy product.

$^1$H-NMR spectrum (CDCl$_3$): δ1.09 (3H, t, J=7 Hz, Cl—CH$_2$CH$_3$), 3.34 (2H, m, —NH—CH$_2$—), 3.33 (1H, C12b—H), 3.78+3.80 (6H, s, OCH$_3$), 5.27 (1H, broad t, CO—NH), 6.52–6.78 (3H, m, C2'—H, C5'—H, C6'—H), 7.0–7.51 (4H, m, aromatic protons), 8.02 (1H, broad s, indole NH) ppm.

The *ethanesulphonate salt* melts at 144°–147° C. (after recrystallization from acetone), [α]$_D^{25}$= −60.7° (c=2.1, water).

Analysis: calculated for C$_{32}$H$_{45}$N$_3$O$_6$S (molecular weight 599.77): C 64.08; H 7.56; N 7.01%. found: C 63.75; H 8.00; N 6.78%.

The *hydrobromide salt* melts at 160°–165° C. (after recrystallization from ethanol).

Example 8

Preparation of (−)-(1S,12bS)-1-ethyl-1,2,3,4,6,7,12,12b-octahydroindolo[2,3-a]quinolizin-1-yl-propionic acid 2-phenylethylamide Starting from 1.34 g. (0.011 moles) of 2-phenylethylamine component, the process described in Example 1 is followed. The crude product is purified by column chromatography on silica gel by using toluene containing 5% of diethylamine as eluant to give 2.41 g (56% yield) of the title compound in the form of a foamy product.

$^1$H-NMR spectrum (CDCl$_3$): δ1.08 (3H, t, J=7 Hz, ClCH$_2$—CH$_3$), 3.32 (1H, C12b—H), 3.36 (2H, m, NH—CH$_2$), 5.20 (1H, broad t, CO—NH), 7.0–7.50 (9H, m, aromatic protons), 7.96 (1H, broad s, indole NH) ppm.

The ethanesulphonate salt melts at 186°–191° C. (after recrystallization from a mixture of isopropanol and diisopropyl ether), [α]$_D^{25}$= −47.5° (c=2.0, water).

Analysis: calculated for C$_{30}$H$_{41}$N$_3$O$_4$S (molecular weight 539.71): C 66.76; H 7.66; N 7.79; S 5.94%. found: C 66.81; H 8.05; N 7.78; S 6.07%.

The hydrobromide salt melts at 180°–190° C. (after recrystallization from isopropanol).

Example 9

Preparation of
(−)-(1S,12bS)-1-ethyl-1,2,3,4,6,7,12,12b-octahydroindolo[2,3-a]quinolizin-1-yl-propionic acid N-methyl-2-hydroxyethylamide Starting from 1.50 g. (0.02 moles) of N-methyl-2-hydroxyethylamine as amine component, the process described in Example 1 is followed. The crude product is purified by column chromatography on silica gel by using toluene containing 15% of methanol as eluant to give 2.20 g. (57% yield) of the title compound as a foamy product.

$^1$H-NMR spectrum (CDCl$_3$): δ1.10 (3H, t, J=7 Hz, Cl—CH$_2$—CH$_3$), 2.66 (3H, s, N—CH$_3$), 3.32 (1H, C12b-H), 3.36+3.63 (2H, m, CH$_2$—OH), 6.95-7.48 (4H, m, aromatic protons), 8.02 (1H, broad s, indole NH) ppm.

The hydrochloride salt melts at 163°-169° C. (after recrystallization from a mixture of isopropanol and diisopropyl ether), $[\alpha]_D^{25} = -81.2°$ (c=1.0, water).

Analysis: calculated for C$_{23}$H$_{34}$ClN$_3$O$_2$ (molecular weight 419.98): C 65.77; H 8.16; N 10.00; Cl (ionic) 8.44%. found: C 65.65; H 8.07; N 9.87; Cl (ionic) 8.64%.

Example 10

Preparation of
(−)-(1S,12bS)-1-ethyl-1,2,3,4,6,7,12,12b-octahydroindolo[2,3-a]quinolizin-1-yl-propionic acid (S)-1-hydroxy-2-butylamide Starting from 1.79 g. (0.02 moles) of (S)-1-hydroxy-2-butylamine as amine component, the process described in Example 1 is followed. The crude product is purified by column chromatography on silica gel by using toluene containing 10% of diethylamine as eluant to give 2.36 g. (59% yield) of the title compound as an oil which crystallizes on standing.

$^1$H-NMR spectrum (CDCl$_3$): δ1.10 (3H, t, J=7 Hz, Cl—CH$_2$—CH$_3$), 0.82 (3H, t, J=7 Hz, NH—CH—CH$_2$—CH$_3$), 3.34 (1H, C12b—H), 3.47 (2H, m, —CH$_2$—OH), 3.68 (1H, m, NH—CH—), 5.27 (1H, broad d, CO—NH), 7.0-7.5 (4H, m, aromatic protons), 8.05 (1H, broad s, indole NH) ppm.

The hydrochloride salt melts at 225°-245° C. (with decomposition) (after recrystallization from isopropanol), $[\alpha]_D^{25} = -80.0°$ (c=2.1, water).

Analysis: calculated for C$_{24}$H$_{36}$ClN$_3$O$_2$ (molecular weight 434.00): C 66.41; H 8.36; N 9.68; Cl (ionic) 8.17%. found: C 65.96; H 8.45; N 9.29; Cl (ionic) 7.78%.

Example 11

Preparation of
(−)-(1S,12bS)-1-ethyl-1,2,3,4,6,7,12,12b-octahydroindolo[2,3-a]quinolizin-1-yl-propionic acid 2-pyridylmethylamide Starting from 1.20 g. (0.011 moles) of 2-pyridylmethylamine as amine component, the process described in Example 1 is followed. The crude product is purified by column chromatography on silica gel by using toluene containing 5% of diethylamine as eluant to give 2.52 g. (62% yield) of the title compound as a foamy product.

$^1$H-NMR spectrum (CDCl$_3$): δ1.06 (3H, t, J=7 Hz, Cl—CH$_2$—CH$_3$), 3.35 (1H, C12b—H), 4.31 (2H, d, $J_{CH2,NH}$=5 Hz, NH—CH$_2$), 6.44 (1H, broad t, CO—NH), 7.0-8.46 (6H, m, aromatic protons+C-3'—H+C5'—H), 7.56 (1H, m, C4'—H), 8.16 (1H, broad s, indole NH), 8.45 (1H, m, C6'—H), ppm.

The ethanesulphonate salt melts at 207°-211° C. (after recrystallization from a mixture of isopropanol and diisopropyl ether), $[\alpha]_D^{25}$=(c=2.0, water).

The hydrochloride salt melts at 168°-178° C. (after recrystallization from isopropanol).

Example 12

Preparation of
(−)-(1S,12bS)-1-ethyl-1,2,3,4,6,7,12,12b-octahydroindolo[2,3-a]quinolizin-1-yl-propionic acid 4-phenylbutylamide Starting from 1.64 g. (0.011 moles) of 4-phenylbutylamine as amine component, the process described in Example 1 is followed. The crude product is purified by column chromatography on silica gel by using toluene containing 5% of diethylamine to give 2.38 g. (52% yield) of the title compound as a foamy product.

$^1$H-NMR spectrum (CDCl$_3$): δ1.07 (3H, t, J=7 Hz, CL—CH$_2$—CH$_3$), 3.33 (1H, C12b—H), 5.20 (1H, broad t, CO—NH), 6.95-7.48 (9H, m, aromatic protons), ppm.

The ethanesulphonate salt melts at 156°-148° C. (after recrystallization from a mixture of isopropanol and diisopropyl ether), $[\alpha]_D^{25} = -58.3°$ (c=2.0, water).

Analysis: calculated for C$_{32}$H$_{45}$N$_3$O$_4$S (molecular weight 567.77): C 67.69; H 7.99; N 7.40%. found: C 67.40; H 8.00; N 7.19%.

The hydrochloride salt melts at 150°-159° C. (after recrystallization from isopropanol).

Example 13

Preparation of
(−)-(1S,12bS)-1-ethyl-1,2,3,4,6,7,12,12b-octahydroindolo[2,3-a]quinolizin-1-yl-propionic acid heptamethyleneimide Starting from 1.24 g. (0.011 moles) of heptamethyleneimine as amine component, the process described in Example 1 is followed. The crude product is purified by column chromatography on silica gel by using toluene containing 5% of diethylamine as eluant to give 1.78 g. (42% yield) of the title compound as a foamy product.

$^1$H-NMR spectrum (CDCl$_3$): δ1.09 (3H, t, J=7 Hz, Cl—CH$_2$—CH$_3$), 3.32 (1H, C12b—H), 6.95-7.47 (4H, m, aromatic protons), 8.10 (1H, broad s, indole NH) ppm.

The hydrochloride salt melts at 201°-238° C. (after recrystallization from acetone), $[\alpha]_D^{25} = -85.4°$ (c=1.0, water).

Analysis: calculated for C$_{27}$H$_{40}$ClN$_3$O (molecular weight 458.06): C 70.79; H 8.80; N 9.17; Cl (ionic) 7.74%. found: C 70.53; H 9.01; N 9.05; Cl (ionic) 7.56%.

The *phosphate salt* melts at 105°-135° C. (with decomposition) (after recrystallization from isopropanol).

Example 14

Preparation of
(−)-(1S,12bS)-1-ethyl-1,2,3,4,6,7,12,12b-octahydroindolo[2,3-a]quinolizin-1-yl-propionic acid diethanolamide Starting from 2.10 g. (0.02 moles) of diethanolamine as amine component, the process described in Example 1 is followed. The crude product is purified by column chromatography on silica gel by using toluene containing 30% of diethylamine as eluant to give 1.74 g. (42% yield) of the title compound as a foamy product.

$^1$H-NMR spectrum (CDCl$_3$): δ1.08 (3H, t, J=7 Hz, Cl—CH$_2$—CH$_3$), 3.29 (1H, C12b—H), 3.25+3.60 (4H, m, two CH$_2$—OH), 6.95-7.48 (4H, m, aromatic protons), 8.08 (1H, broad s, indole NH) ppm.

$^{13}$C-NMR spectrum (CDCl$_3$): δ7.95 (Cl—CH$_2$—CH$_3$), 21.81 (C7), 21.81 (C3), 27.70* (C13), 29.03* (C12), 30.30 (Cl—CH$_2$—CH$_3$), 34.60 (C2), 39.72 (Cl), 50.48 and 52.12 (two N—CH$_2$), 54.26 (C6), 56.87 (C4), 60.37 and 61.09 (two CH$_2$—OH), 66.87 (C12b), 111.02 (C11), 111.07 (C7a), 117.72 (C8), 119,48 (C9), 121.65 (C10), 126.71 (C7b), 134.12 (C12a), 136.09 (C11a), 176.16 (NCO) ppm (*: exchangeable).

The *hydrobromide salt* decomposes from 135° C. (after recrystallization from ethyl acetate), [α]$_D^{25}$= −62.9° (c=2.0, water).

Analysis: calculated for C$_{24}$H$_{36}$BrN$_3$O$_3$ (molecular weight 494.46) C 58.29; H 7.34; N 8.50; Br (ionic) 16.16%. found: C 57.72; H 7.42; N 8.29; Br (ionic) 16.06%.

Example 15

Preparation of
(−)-(1S,12bS)-1-ethyl-1,2,3,4,6,7,12,12b-octahydroindolo[2,3-a]quinolizin-1-yl-propionic acid 2-hydroxyethylamide Starting from 0.67 g. (0.011 moles) of ethanolamine as amine component, the process described in Example 1 is followed. The crude product is purified by column chromatography on silica gel by using toluene containing 30% of diethylamine as eluant to give 1.47 g. (40% yield) of the title compound as a foamy product.

$^1$H-NMR spectrum (CDCl$_3$): δ1.10 (3H, t, J=7 Hz, Cl—CH$_2$—CH$_3$), 3.34 (1H, C12b—H), 3.55 (2H, t, J=5 Hz, CH$_2$—OH), 5.68 (1H, broad t, CO—NH), 7.0-7.49 (4H, aromatic protons), 7.88 (1H, broad s, indole NH) ppm.

The *hydrobromide salt* melts at 169°-179° C. (with decomposition) after recrystallization from isopropanol), ]α]$_D^{26}$= −67.7° (c=1.0, water).

Analysis: calculated for C$_{22}$H$_{32}$BrN$_3$O$_2$ (molecular weight 450.41) C 58.66; H 7.16; N 9.33; Br (ionic) 17.74%. found: C 58.42; H 7.41; N 9.45; Br (ionic) 16.82%.

The *hydrochloride salt* melts at 164°-178° C. (after recrystallization from isopropanol).

Example 16

Preparation of
(−)-(1S,12bS)-1-ethyl-1,2,3,4,6,7,12,12b-octahydroindolo[2,3-a]quinolizin-1-yl-propionic acid 3-methoxypropylamide Starting from 0.98 g. (0.011 moles) of 3-methoxypropylamine as amine component the process described in Example 1 is followed. The crude product is purified by column chromatography by using toluene containing 20% of diethylamine as eluant to give 2.39 g. (60% yield) of the title compound as a foamy product.

$^1$H-NMR spectrum (CDCl$_3$): δ1.08 (3H, t, J=7 Hz, Cl—CH$_2$—CH$_3$), 3.35 (1H, C12b—H), 3.12 (2H, t, J=6 Hz, CH$_2$—OCH$_3$), 3.17 (3H, s, OCH$_3$), 5.76 (1H, broad t, CO—NH), 7.0-7.47 (4H, m, aromatic protons), 8.07 (1H, broad s, indole NH), ppm.

The *hydrochloride salt* melts at 144°-149° C. after recrystallization from isopropanol), [α]$_D^{26}$=72.5° (c=1.0, water).

Analysis: calculated for C$_{24}$H$_{36}$ClN$_3$O$_2$ (molecular weight 434.00) C 66.41; H 8.36; N 9.68; Cl (ionic) 8.17%. found: C 66.47; H 7.71; N 9.52; Cl (ionic) 8.17%.

Example 17

Preparation of
(−)-(1S,12bS)-1-ethyl-1,2,3,4,6,7,12,12b-octahydroindolo[2,3-a]quinolizin-1-yl-propionic acid (DL)-2-hydroxypropylamide Starting from 0.83 g. (0.011 moles) of (DL)-2-hydroxypropylamine as amine component, the process described in Example 1 is followed. The crude product is purified by column chromatography on silica gel by using toluene containing 30% of diethylamine as eluant to give 1.60 g. (42% yield) of the title compound as a foamy product.

$^1$H-NMR spectrum (CDCl$_3$): δ1.08 (3H, t, J=7 Hz, Cl—CH$_2$—CH$_3$) 1.02 (3H, d, J 2 7 Hz, OH—CH—CH$_3$), 3.33 (1H, C12b—H), 3.71 (1H, m, CH—OH), 5.82 (1H, broad t, CO—NH), 6.95-7.49 (4H, m, aromatic protons), 8.05 (1H, broad s, indole NH) ppm.

The *hydrochloride salt* melts at 175°-181° C. (after recrystallization from isopropanol), [α]$_D^{26}$= −75.4° (c=1.0, water).

Analysis: calculated for C$_{23}$H$_{34}$ClN$_3$O$_2$ (molecular weight 419.98): C 65.77; H 8.16; N 10.01; Cl (ionic) 8.44%. found: C 65.48; H 8.12; N 9.86; Cl (ionic) 8.22%.

The *hydrobromide salt* melts at 184°-191° C. (after recrystallization from isopropanol).

The *ethanesulphonate salt* melts at 185°-200° C. (after recrystallization from acetone).

Example 18

Preparation of
(−)-(1S,12bS)-1-ethyl-1,2,3,4,6,7,12,12b-octahydroindolo[2,3-a]quinolizin-1-yl-propionic acid cyclopropylamide Starting from 0.63 g. (0.011 moles) of cyclopropylamine as amine component, the process described in Example 1 is followed. The crude product is purified by column chromatography on silica gel by using toluene containing 20% of diethylamine as eluant to give 2.15 g. (59% yield) of the title compound as a foamy product.

$^1$H-NMR spectrum (CDCl$_3$): δ1.10 (3H, t, J=7 Hz, Cl—CH$_2$—CH$_3$), 3.34 (1H, C12b—H), 0.15-0.8 (4H, broad s, CO—NH), 7.0-7.5 (4H, m, aromatic protons), 8.0 (1H, broad s, indole NH) ppm.

The *ethanesulphonate salt* melts at 160°-167° C. (after recrystallization from acetone), [α]$_D^{26}$= −65.7 (c=2.0, water).

Analysis: calculated for C$_{25}$H$_{37}$N$_3$O$_4$S (molecular weight 475.63): C 63.13; H 7.84; N 8.83; S 6.74% found C 62.72; H 8.15; N 8.74; S 6.73%.

The *hydrobromide salt* melts at 193°-200° C. (after recrystallization from ethanol).

Example 19

Preparation of
(−)-(1S,12bS)-1-ethyl-1,2,3,4,6,7,12,12b-octahydroindolo[2,3-a]quinolizin-1-yl-propionic acid N-ethyl-2-hydroxy-ethylamide Starting from 0.98 g. (0.011 moles) of N-ethyl-2-hydroxyethylamine as amine component, the process described in Example 1 is followed. The crude product is purified by recrystallization from isopropanol to give 2.44 g. (61% yield) of the title compound, m.p.: 199°–202° C.

¹H-NMR spectrum (CDCl₃): δ1.09 (3H, t, J=7 Hz, Cl—CH₂—CH₃), 0.71+0.98 (3H, t, J=7 Hz, N—CH₂—CH₃), 3.30 (1H, C12b—H), 3.6 (2H, m, CH₂—OH), 6.95–7.48 (4H, m, aromatic protons), 8.02 and 8.10 (1H, broad s, indole NH) ppm.

The *hydrobromide salt* melts at 235°–239° C. (with decomposition) (after recrystallization from the mixture of isopropanol and diisopropyl ether), [α]$_D^{26}$ = −77.9° (c=2.0, water).

Analysis: calculated for C₂₄H₃₆BrN₃O₂ (molecular weight 478.46): C 60.24; H 7.58; N 8.78; Br (ionic) 16.70%. found: C 60.29; H 7.55; N 8.59; Br (ionic) 16.52%;

Example 20

Preparation of
(−)-(1S,12bS)-1-ethyl-1,2,3,4,6,7,12,12b-octahydroindolo[2,3-a]quinolizin-1-yl-propionic acid allylamide Starting from 0.63 g. (0.011 moles) of allylamine as amine component, the process described in Example 1 is followed. The crude product is purified by column chromatography on silica gel by using toluene containing 10% of diethylamine as eluant to give 1.50 g. (41% yield) of the title compound as a foamy product.

¹H-NMR spectrum (CDCl₃): δ1.09 (3H, t, J=7 Hz, Cl—CH₂—CH₃), 3.35 (1H, C12b-H), 3.71 (2H, m, NH—CH₂), 5.03 and 5.06 (2H, m, =CH₂), 5.20 (1H, broad t, NH—CH₂), 5.71 (1H, m, —CH=), 6.95–7.49 (4H, m, aromatic protons), 7.94 (1H, broad s, indole NH) ppm.

The *methanesulphonate salt* melts at 257°–261° C. (after recrystallization from isopropanol), [α]$_D^{26}$ = −74.2° (c=2.0, water).

Analysis: calculated for C₂₄H₃₅N₃O₄S (molecular weight 461.61): C 62.44; H 5.64; N 9.10; S 6.95%. found: C 62.39; H 7.99; N 8.70; S 6.65%.

Example 21

Preparation of
(−)-(1S,12bS)-1-ethyl-1,2,3,4,6,7,12,12b-octahydroindolo[2,3-a]quinolizin-1-yl-propionic acid 2-methoxyethylamide Starting from 0.83 g. (0.11 moles) of 2-methoxyethylamine as amine component, the process described in Example 1 is followed. The crude product is purified by column chromatography on silica gel by using toluene containing 10% of diethylamine as eluant to give 2.22 g. (58% yield) of the title compound as a foamy product.

¹-NMR spectrum (CDCl₃): δ1.10 (3H, t, J=7 Hz, Cl—CH₂—CH₃), 3.25 (3H, s, OCH₃) 3.32 (1H, C12b—H), 3.3 (4H, m, NH—CH₂+CH₂—OCH₃) 5.48 (1H, broad t, CO—NH), 6.95–7.50 (4H, m, aromatic protons), 7.99 (1H, broad s, indole NH) ppm.

The *hydrobromide salt* melts at 159°–163° C. (with decomposition) (after recrystallization from isopropanol), [α]$_D^{26}$=31 65.0° (c=2.0, water).

Analysis: calculated for C₂₃H₃₄BrN₃O₂ (molecular weight 464.43): C 59.48; H 7.38; N 9.05; Br (ionic) 17.21%. found: C 59.29; H 7.82; N 8.97; Br (ionic) 16.88%.

The *ethanesulphonate salt* melts at 206°–214° C. (after recrystallization from isopropanol).

The *hydrochloride salt* melts at 148°–155° C. (after recrystallization from isopropanol).

Example 22

Preparation of
(−)-(1S,12bS)-1-ethyl-1,2,3,4,6,7,12,12b-octahydroindolo[2,3-a]quinolizin-1-yl-propionic acid dibenzylamide Starting from 2.17 g. (0.011 moles) of dibenzylamine as amine component, the process described in Example 1 is followed. The crude product is purified by recrystallization from isopropanol to give 2.48 g. (49% yield) of the title compound, m.p. 140°–142° C.

Analysis: calculated for C₃₄H₃₉N₃O (molecular weight 505.67): C 80.75; H 7.77; N 8.31%. found: C 80.66; H 7.80; N 8.17%.

¹H-NMR spectrum (CDCl₃): δ1.05 (3H, t, J=7 Hz, Cl—CH₂—CH₃), 3.28 (1H, C12b—H), 3.95–4.35 (4H, broad s, two N—CH₂), 6.8–7.45 (14H, m, aromatic protons), 7.92 (1H, broad s, indole NH) ppm.

The *methanesulphonate salt* melts at 205°–215° C. (after recrystallization from a mixture of isopropanol and diisopropyl ether), [α]$_D^{26}$ = −71.3° (c=2.0, water).

Analysis: calculated for C₃₅H₄₃N₃O₄S (molecular weight 601.78): C 69.85; H 7.20; N 6.98; S 5.33%; found: C 69.61; H 7.04; N 6.83; S 5.043%.

The *ethanesulphonate salt* melts at 188°–205° C. (after recrystallization from isopropanol).

Example 23

Preparation of
(−)-(1S,12bS)-1-ethyl-1,2,3,4,6,7,12,12b-octahydroindolo[2,3-a]quinolizin-1-yl-propionic acid 3-hydroxypropylamide Starting from 0.83 g. (0.011 moles) of 3-hydroxypropylamine as amine component, the process described in Example 1 is followed. The crude product is purified by column chromatography on silica gel by using dichloromethane containing 10% of diethylamine as eluant to give 2.58 g. (67% yield) of the title compound as an oil which becomes crystalline on standing.

¹H-NMR spectrum (CDCl₃): δ1.09 (3H, t, J=7 Hz, Cl—CH₂—CH₃), 3.36 (1H, C12b—H), 3.59 (2H, t, J=5 Hz, CH₂—OH), 6.08 (1H, broad t, CO—NH), 6.95–7.49 (4H, m, aromatic protons), 8.23 (1H, broad s, indole NH) ppm.

The *hydrochloric salt* melts at 219°–229° C. (after recrystallization from isopropanol), [α]$_D^{26}$ = −76.4° (c=2.0, water).

Analysis: calculated for C₂₃H₃₄ClN₃O₂ (molecular weight 419.98): C 65.77; H 8.16; N 10.01; Cl (ionic) 8.44%. found: C 65.92; H 8.24% N 9.92; Cl (ionic) 8.61%.

The *ethanesulphonate salt* melts at 200°–218° C. (after recrystallization from isopropanol).

Example 24

Preparation of
(−)-(1S,12bS)-1-ethyl-1,2,3,4,6,7,12,12b-octahydroindolo[2,3-a]quinolizin-1-yl-propionic acid 2,4-dimethoxybenzylamide Starting from 1.84 g. (0.011 moles) of 2,4-dimethoxybenzylamine as amine component, the process described in Example 1 is followed. The crude product is purified by column chromatography on silica gel by using toluene containing 10% of diethylamine as eluant to give 2.84 g. (59% yield) of the aimed compound as a foamy product.

¹H-NMR spectrum (CDCl₃): δ1.08 (3H, t, J=7 Hz, Cl—CH₂—CH̲₃), 3.34 (1H, C12b—H), 3.59+3.73 (6H, s, two OCH₃), 4.23 (2H, d, $J_{CH_2,NH}$=5 Hz), 5.61 (1H, broad t, CO—NH̲), 6.39 (2H, m, C3'—H+C5'—H), 6.95-7.48 (5H, m, aromatic protons+C6'—H), 7.99 (1H, broad s, indole NH) ppm.

The *ethanesulphonate salt* melts at 215°-219° C. (after recrystallization from a mixture of isopropanol and diisopropyl ether), $[\alpha]_D^{26}$=−53.1° (c=2.0, water).

Analysis: calculated for C₃₁H₄₃N₃O₆S (molecular weight 585.74): C 63.56; H 7.40; N 7.17; S 5.47%. found: C 63.32; H 7.22; N 7.23; S 5.60%.

Example 25

Preparation of
(−)-(1S,12bS)-1-ethyl-1,2,3,4,5,6,7,12,12b-octahydroindolo[2,3-a]quinolizin-1-yl-propionic acid anilide 3.26 g. (0.01 moles) of (−)-(1S,12bS)-1-ethyl-1,2,3,4,6,7,12,12b-octahydroindolo[2,3-a]quinolizin-1-yl-propionic acid are added to a solution containing 2.04 g. (0.02 moles) of N-methylmorpholine (redistilled from sodium) in 20 ml. of dry tetrahydrofuran while stirring under nitrogen, then the solution is cooled to −5° C. and 1.10 g. (0.01 mole) of ethyl chloroformate are rapidly dropped in while stirring vigorously and keeping the inner temperature at or lower than 0° C. The mixture is stirred at 0° C. for 30 minutes, then a mixture containing 1.86 g. (0.02 moles) of aniline in 10 ml of dry tetrahydrofuran is dropwise added at a temperature between −5° C. and 0° C. during 10 minutes. Then the mixture is stirred at 0° C. for 30 minutes and during an additional stirring for 4 hours the temperature of the mixture is allowed to warm to room temperature. The mixture is evaporated on a rotating evaporator. After shaking thoroughly the evaporation residue with 50 ml of dichloromethane and 50 ml. of water, the product (which is the water- and dichloromethane-insoluble hydrochloride of the formed product) is filtered, washed thoroughly with dichloromethane and water and suspended in the mixture of 25 ml of water and 25 ml of dichloromethane. This mixture is made alkaline by adding cautiously 4.24 g. (0.04 moles) of sodium carbonate under vigorous stirring. After dissolution of the product, the phases are separated, the dichloromethane layer is washed three times with 10 ml. of water each, dried over anhydrous magnesium sulphate and evaporated to give 2.69 g. (67% yield) of the title compound which melts at 159°-163° C. after recrystallization from toluene.

¹H-NMR spectrum (CDCl₃): δ1.08 (3H, t, J=7 Hz. Cl—CH₂—CH̲₃), 3.33 (1H, C12b—H), 6.92 (1H, broad s, CO—NH̲), 7.0-7.51 (9H, m, aromatic protons), 7.92 (1H, broad s, indole NH) ppm.

The *methanesulphonate salt* melts at 167°-170° C. (after recrystallization from a water), $[\alpha]_D^{25}$=−86.2° (c=2.0, ethanol).

Analysis: calculated for C₂₇H₃₅N₃O₄S (molecular weight 497.64): C 65.16; H 7.09; N 8.44; S 6.44%. found: C 64.90; H 6.89; N 8.60; S 6.44%.

The *hydrochloride salt* melts gradually between 200° and 250° C. (after recrystallization from ethanol).

¹H-NMR spectrum (CDCl₃+DMSO): 1.07 (3H, t, J=7 Hz, Cl—CH₂—CH̲₃), 4.46 (1H, C12b—H), 6.86-7.70 (9H, m, aromatic protons), 9.6 (1H, broad s, CO—NH̲), 9.78 (1H, broad s, indole NH) ppm.

¹³C-NMR spectrum (CDCl₃+DMSO): δ7.97 (Cl—CH₂—CH̲₃), 18.67 (C3), 18.67 (C7), 28.79* (C13), 30.03* (C14), 30.71° (Cl—CH̲₂—CH₃), 31.65° (C2), 39.85 (C12b), 54.70 (C6), 55.33 (C4), 67.46 (C13b), 108.71 (C7a), 112.54 (C11), 117, 78 (C8), 119.63 (C9), 122.46 (C10), 125,46 (C12a), 126.56 (C7b), 137.33 (C11a), 119.63+128.34+123.21+139.05 (Ph carbons), 171.81 (NCO) ppm (*, o: exchangeable).

The *ethanesulphonate salt* melts at 157°-161° C. (after recrystallization from water).

The *citrate salt* melts at 136°-140° C. (after recrystallization from water).

The *D-tartrate salt* melts at 135°-140° C. (after recrystallization from water).

The hydrobromide salt melts at 203°-212° C. (after recrystallization from isopropanol).

The phosphate *salt* melts at 160°-167° C. (after recrystallization from isopropanol).

Example 26

Preparation of
(−)-(1S,12bS)-1-ethyl-1,2,3,4,6,7,12,12b-octahydroindolo[2,3-a]quinolizin-1-yl-propionic acid 4-chlorobenzylamide The process described in Example 25 is followed, except that 1.56 g. (0.011 moles) of 4-chlorobenzylamine are used as amine component to give 2.56 g. (57% yield) of the title compound as an oil, which becomes crystalline on standing.

¹H-NMR spectrum (CDCl₃): 1.10 (3H, t, J=7 Hz, Cl—CH₂—CH̲₃), 3.33 (1H, C12b—H), 4.20 (2H, d, $J_{CH_2,NH}$=5 Hz, NH—CH̲₂), 5.51 (1H, broad t, CO—NH̲), 7.0-7.48 (8H, m, aromatic protons), 7.94 (1H, broad s, indole NH) ppm.

The *phosphate salt* melts at 155°-158° C. (after recrystallization from isopropanol), $[\alpha]_D^{25}$=−65.9° (c=2.0, water).

The *ethanesulphonate salt* melts at 141°-145° C. (after recrystallization from a mixture of isopropanol and diisopropyl ether).

The *hydrochloride salt* melts at 227°-240° C. (after recrystallization from isopropanol).

Example 27

Preparation of
(−)-(1S,12bS)-1-ethyl-1,2,3,4,6,7,12,12b-octahydroindolo[2,3-a]quinolizin-1-yl-propionic acid 4-methylbenzylamide The process described in Example 25 is followed, except that 1.34 g. (0.015 moles) of 4-methylbenzylamine are used as amine component to give 2.61 g. (61% yield) of the title compound which slowly becomes crystalline on standing.

¹H-NMR spectrum (CDCl₃): δ1.08 (3H, t, J=7 Hz, Cl—CH₂—CH̲₃), 2.27 (3H, s, Ph—CH̲₃), 3.33 (1H, C12b—H), 4.22 (2H, d, $J_{CH_2,NH}$=5 Hz, NH—CH̲₂), 5.52 (1H, broad t, CO—NH̲), 6.95-7.47 (8H, m, aromatic protons), 8.0 (1H, broad s, indole NH) ppm.

The *phosphate salt* melts gradually from 85° C. (with decomposition) (after recrystallization from isopropanol), $[\alpha]_D^{25}$=−65.3° (c=2.0, water).

The *hydrochloride salt* melts at 220°-242° C. (after recrystallization from isopropanol).

The *methanesulphonate salt* melts at 140°-148° C. (after recrystallization from a mixture of isopropanol and diisopropyl ether).

Example 28

Preparation of
(−)-(1S,12bS)-1-ethyl-1,2,3,4,6,7,12,12b-octahydroindolo[2,3-a]quinolizin-1-yl-propionic acid 4-methylanilide The process described in Example 25 is followed, except that 1.18 g. (0.011 moles) of 4-methylaniline are used as amine component to give 2.54 g. (61% yield) of the title compound which can further be purified by recrystallization from isopropanol.

$^1$H-NMR spectrum (CDCl$_3$): δ1.09 (3H, t, J=7 Hz, C1—CH$_2$—CH$_3$), 1.78 (2H, q, J=7 Hz, C1—CH$_2$—CH$_3$), 2.23 (3H, s, Ph—CH$_3$), 3.35 (1H, C12b—H), 6.80 (1H, broad s, CO—NH), 7.0-7.50 (4H, m, aromatic protons), 7.0 (2H, m, C3'—H++C5'—H), 7.20 (2H, m, C2'—H+C6'—H), 7.92 (1H, broad s, indole NH) ppm.

The *methanesulphonate salt* melts at 196°-199° C. (after recrystallization from isopropanol), $[\alpha]_D^{26}=-92.3°$ (c=1.0, ethanol).

Analysis: calculated for C$_{28}$H$_{37}$N$_3$O$_4$S (molecular weight 511.66): C 65.72; H 7.29; N 8.21; S 6.27%. found: C 65.36; H 6.95; N 8.15; S 6.28%.

The *hydrochloride salt* melts at 147°-159° C.

Example 29

Preparation of
(−)-(1S,12bS)-1-ethyl-1,2,3,4,6,7,12,12b-octahydroindolo[2,3-a]quinolizin-1-yl-propionic acid 3-trifluoromethylanilide The process described in Example 25 is followed, except that 1.77 g. (0.011 moles) of 3-trifluoromethylaniline are used as amine component to give 3.2 g. (68% yield) of the title compound which melts at 154°-155.5° C. after recrystallization from a mixture of toluene and n-hexane, $[\alpha]_D^{26}=-135.5°$ (c=2.0, ethanol).

Analysis: calculated for C$_{27}$H$_{30}$F$_3$N$_3$O (molecular weight 469.53): C 69.06; H 6.44; N 8.95%. found: C 69.04; H 6.56; N 8.95%.

$^1$H-NMR spectrum (CDCl$_3$): δ1.10 (3H, t, J=7 Hz, C1—CH$_2$—CH$_3$), 1.76 (2H, q, J=7 Hz, C1—CH$_2$—CH$_3$), 3.34 (1H, C12b—H), 6.90 (1H, broad s, CO—NH), 7.0-7.60 (8H, m, aromatic protons+C-2'—H+C4'—H+C5'—H), 7.86 (1H, broad s, indole NH) ppm.

The *hydrochloric salt* melts at 214°-226° C.

The *methanesulphonate salt* melts at 220°-228° C. (after recrystallization from isopropanol).

Example 30

Preparation of
(−)-(1S,12bS)-1-ethyl-1,2,3,4,6,7,12,12b-octahydroindolo[2,3-a]quinolizin-1-yl-propionic acid 4-methoxyanilide The process described in Example 25 is followed except that 1.35 g. (0.011 moles) of 4-methoxyaniline are used as amine component to give 2.66 g. (62% yield) of the title compound as a foamy product.

$^1$H-NMR spectrum (CDCl$_3$): δ1.08 (3H, t, J=7 Hz, C1—CH$_2$—CH$_3$), 1.76 (2H, q, J=7 Zh, C1—CH$_2$—CH$_3$), 3.33 (1H, C12b—H), 6.91 (1H, broad s, CO—NH), 6.95-7.55 (13H, m, aromatic protons), 7.89 (1H, broad s, indole NH) ppm.

The *methanesulphonate salt* melts at 190°-197° C. (after recrystallization from isopropanol), $[\alpha]_D^{26}=-88.9°$ (c=1.0, ethanol).

Analysis: calculated for C$_{28}$H$_{37}$N$_3$O$_5$S (molecular weight 527.66): C 63.73; H 7.07; N 7.96; S 6.08%. found: C 63.57; H 6.98; N 7.89; S 6.10%.

Example 31

Preparation of
(−)-(1S,12bS)-1-ethyl-1,2,3,4,6,7,12,12b-octahydroindolo[2,3-a]quinolizin-1-yl-propionic acid 4-phenylanilide The process described in Example 25 is followed, except that 1.86 g. (0.011 moles) of 4-aminobiphenyl are used as amine component to give 2.93 g. (61% yield) of the title compound melting at 97°-105° C. after recrystallization from toluene, $[\alpha]_D^{26}=-152.3°$ (c=2.0, ethanol).

Analysis: calculated for C$_{32}$H$_{35}$N$_3$O (molecular weight 477.62): C 80.47; H 7.39; N 8.80%. found: C 81.06; H 7.65; N 8.90%.

$^1$H-NMR (CDCl$_3$): δ1.08 (3H, t, J=7 Hz, C1—CH$_2$—CH$_3$), 1.76 (2H, q, J=7 Hz, C1—CH$_2$—CH$_3$), 3.33 (1H, C12b—H), 6.91 (1H, broad s, CO—NH), 6.95-7.55 (13H, m, aromatic protons), 7.89 (1H, broad s, indole NH) ppm.

The *hydrochloride salt* melts at 257°-271° C.

The *methanesulphonate salt* melts at 220°-244° C. (after recrystallization from isopropanol).

Example 32

Preparation of
(−)-(1S,12S)-1-ethyl-1,2,3,4,6,7,12,12b-octahydroindolo[2,3-a]quinolizin-1-yl-propionic acid 4-acetylanilide The process described in Example 25 is followed except that 1.49 g. (0.011 moles) of 4-aminoacetophenone are used as amine component to give 1.45 g. (33% yield) of the title compound as a foamy product.

$^1$H-NMR spectrum (CDCl$_3$): δ1.11 (3H, t, J=7 Hz, C1—CH$_2$—CH$_3$), 1.79 (2H, q, J=7 Hz, C1—CH$_2$—CH$_3$), 2.47 (3H, s, CO—CH$_3$), 3.36 (1H, C12b—H), 7.03 (1H, broad s, CO—NH), 7.0-7.52 (4H, m, aromatic protons), 7.39 (2H, m, C2'—H+C6'—H), 7.82 (2H, m, C3'—H+C5'—H), 7.88 (1H, broad s, indole NH) ppm.

The *hydrochloride salt* melts at 164°-173° C.

Example 33

Preparation of
(−)-(1S,12bS)-1-ethyl-1,2,3,4,6,7,12,12b-octahydroindolo[2,3-a]quinolizin-1-yl-propionic acid 4-hydroxybenzylamide The process described in Example 25 is followed, except that 1.35 g. (0.011 moles) of 4-hydroxybenzylamine are used as amine component to give 2.41 g. (56% yield) of the title compound as a foamy product.

$^1$H-NMR spectrum (CDCl$_3$): δ1.06 (3H, t, J=7 Hz, C1—CH$_2$—CH$_3$), 3.32 (1H, C12b—H), 4.14 (2H, d, $J_{CH_2,NH}=5$ Hz, NH—CH$_2$), 5.45 (1H, broad s, OH), 5.63 (1H, broad t, CO—NH), 6.65 (2H, m, C3'—H+C-5'—H), 6.90 (2H, m, C2'—H), 7.0-7.47 (4H, m, aromatic protons), 7.96 (1H, broad s, indole NH) ppm.

The *ethanesulphonate salt* melts at 152°-160° C. (with decomposition) (after recrystallization from isopropanol), $[\alpha]_D^{26}=-59.6°$ (c=1.0, water).

Analysis: calculated for C₂₉H₃₉N₃O₅S (molecular weight 541.69): C 64.33; H 7.26; N 7.76; S 5.92% found: C 64.59; H 7.50; N 7.69; S 5.82%.

The *methanesulphonate salt* melts at 157°–164° C. (after recrystallization for isopropanol).

Example 34

Preparation of
(−)-(1S,12bS)-1-ethyl-1,2,3,4,6,7,12,12b-octahydro-indolo[2,3-a]quinolizin-1-yl-acetic acid benzylamide 3.12 g. (0.01 mole) of (−)-(1S,12bS)-1-ethyl-1,2,3,4,6,7,12,12b-octahydro-indol[2,3-a]quinolizin-1-yl-acetic acid are added to a solution containing 2.04 g. (0.02 moles) of N-methylmorpholine (redistilled from sodium) in 20 ml. of dry tetrahydrofuran while stirring under nitrogen, then the solution is cooled to −5° C. and 1.10 g. (0.01 mole) of ethyl chloroformate are rapidly dropped in while stirring vigorously and keeping the inner temperature at or lower than 0° C. The mixture is stirred at 0° C. for 30 minutes, then a mixture containing 1.18 g. (0.011 moles) of benzylamine in 10 ml of dry tetrahydrofuran is dropwise added at a temperature between −5° C. and 0° C. during 10 minutes. The mixture is stirred at 0° C. for 30 minutes and then during an additional stirring for 4 hours the temperature of the mixture is allowed to warm to room temperature. The mixture is evaporated on a rotating evaporator. After shaking thoroughly the residue with 50 ml. of dichloromethane and 20 ml. of water, the phases are separated. The dichloromethane solution is washed with 20 ml. of 5% sodium carbonate solution and then three times with 20 ml of water each, dried over anhydrous magnesium sulphate and evaporated. The residue which is the crude product, is purified by column chromatography on silica gel by using toluene containing 10% of diethylamine as eluant to give 1.89 g. (44% yield) of the title product which can further be purified by recrystallization from benzene, m.p. 179°–180° C.

¹H-NMR (CDCl₃): δ1.15 (3H, t, J=7 Hz, Cl—CH₂—CH₃), 3.70 and 4.24 (2H, dd each, $J_{gem}$=15 Hz, $J_{CH_2NH}$=5+7 Hz, Ph—CH₂), 3.34 (1H, C12b—H), 5.80 (1H, broad t, CO—NH), 7.0–7.49 (9H, m, aromatic protons), 7.92 (1H, broad t, indole NH), 2.20 and 2.62 (2H, d, $J_{gem}$==14.5 Hz, CO—CH₂) ppm.

The *D-tartrate salt* melts at 112°–116° C. (after recrystallization from isopropanol), [α]_D²⁵= −55° (c=1.0, ethanol).

Analysis: calculated for C₃₀H₃₇N₃O₇ (molecular weight 551.62): C 65.32; H 6.76; N 7.62%. found: C 64.92; H 6.71; N 7.61%.

Example 35

Preparation of
(−)-(1S,12bS)-1-ethyl-1,2,3,4,6,7,12,12b-octahydroindole[2,3-a]quinolizin-1-yl-acetic acid anilide The process described in Example 34 is followed, except that 1.02 g. (0.011 moles) of aniline are used as amine component. The crude product is purified by column chromatography on silica gel by using toluene containing 5% of diethylamine as eluant to give 1.47 g. (38% yield) of the title compound as a foamy product.

¹H-NMR-spectrum (CDCl₃): δ1.16 (3H, t, J=7 Hz, Cl—CH₂—CH₃), 2.34+2.68 (2H, d, $J_{gem}$=14.5 Hz, CO—CH₂), 3.40 (1H, C12b—H), 6.95–7.47 (9H, m, aromatic protons), 7.75 (1H, broad s, CO—NH), 7.88 (1H, broad s, indole NH) ppm.

The *methanesulphonate salt* melts at 172°–180° C. (after recrystallization from isopropanol), [α]_D²⁵= −164° (c=1.0, methanol).

Analysis: calculated for C₂₆H₃₃N₃O₄S (molecular weight 483.61): C 64.57; H 6.28; N 8.69; S 6.63%. found: C 64.44; H 6.64; N 8.62; S 6.82%.

Example 36

Preparation of
(−)-(1S,12bS)-1-ethyl-1,2,3,4,6,7,12,12b-octahydroindolo[2,3-a]quinolizin-1-yl-acetic acid (S)-1-phenylethylamide The process described in Example 34 is followed, except that 1.33 g. (0.011 moles) of (S)-1-phenylethylamine are used as amine component. The crude product is purified by column chromatography on silica gel by using toluene containing 5% of diethylamine as eluant to give 1.66 g. (40% yield) of the title compound which can further be purified by recrystallization from ethanol, m.p.: 188°–192° C.

¹H-NMR spectrum (CDCl₃): δ1.10 (3H, t, J=7 Hz, Cl—CH₂—CH₃), 1.34 (3H, d, J=7 Hz, NH—CH—CH₃), 3.35 (1H, C12b—H), 4.91 (1H, m, NH—CH), 5.87 (1H, d, $J_{NH,CH}$=7 Hz, (CO—NH) 7.0–7.48 (9H, m, aromatic protons), 7.85 (1H, broad s, indole NH), 2.58 and 2.83 (2H, d, $J_{gem}$=0 Hz, CO—CH₂) ppm.

The phosphate salt decomposed from 130° C. (after recrystallization from isopropanol), [α]_D²⁵= −125° (c=1.0, methanol).

Example 37

Preparation of
(−)-(1S,12bS)-1,ethyl-1,2,3,4,6,7,12,12b-octahydroindolo[2,3-a]quinolizin-1-yl-acetic acid (R)-1-phenylethylamide The process described in Example 34 is followed, except that 1.33 g. (0.011 moles) of (R)-1-phenylethylamine are used as amine component. The crude product is purified by column chromatography on silica gel by using toluene containing 5% diethylamine as eluant to give 1.67 g. (40% yield) of the title compound which can further be purified by recrystallization from ethanol, m.p.: 138°–142° C.

¹H-NMR spectrum (CDCl₃): δ1.08 (3H, d, J=7 Hz, NH—CH—CH₃), 1.12 (3H, t, J=7 Hz, Cl—CH₂—CH₃), 2.27 and 2.61 (2H, d, $J_{gem}$=15.0 Hz, CO—CH₂), 3.32 (1H, C12b—H), 4.78 (1H, m, NH—CH), 5.78 (1H, d, $J_{NH,CH}$=7 Hz, CO—NH), 7.0–7.50 (9H, m, aromatic protons), 7.91 (1H, broad s, indole NH) ppm.

The *phosphate salt* decomposes from 140° C. (after recrystallization from isopropanol), [α]_D²⁶=(c=1.0, methanol).

Example 38

Preparation of
(−)-(1S,12bS)-1-ethyl-1,2,3,4,6,7,12,12b-octohydroindolo[2,3-a]quinolizin-1-yl-acetic acid heptamethyleneimide The process described in Example 34 is followed except that 1.24 g. (0.011 moles) of heptamethyleneimine are used as amine component. The crude product is purified by column chromatography on silica gel by using toluene containing 5% of diethylamine as eluant to give 1.84 g. (45% yield) of the title compound which can further be purified by recrystallization from ethanol, m.p.: 137°-139° C.

$^1$H-NMR spectrum (CDCl$_3$): 1.15 (3H, t, J=7 Hz, Cl—CH$_2$—C$\underline{H}_3$), 2.35 and 2.66 (2H, d, J$_{gem}$=15.0 Hz, CO—CH$_2$), 3.32 (1H, C12b—H), 3.0-3.4 (4H, m, two N—C$\underline{H}_2$) 6.95-7.48 (4H, m, aromatic protons), 7.97 (1H, broad s, indole NH) ppm.

The *hydrochloride salt* decomposes from 195° C. (after recrystallization from a mixture of dioxane and diethyl ether), [α]$_D^{25}$=−151° (c=1.0, methanol), Analysis: Calculated for C$_{26}$H$_{38}$ClN$_3$O (molecular weight 444.04): C 70.33; H 8.63; Cl (ionic) 8.00; N 9.45%. found: C 69.72; H 8.36; Cl (ionic) 8.31; n 9.16%.

Example 39

Preparation of
(+)-trans-1-ethyl-1,2,3,4,6,7,12,12b-octahydroindolo[2,3-a]quinolizin-1-yl-propionic acid N-methyl-2-hydroxyethylamide 3.26 g. (0.01 mole) of (+)-trans-1-ethyl-1,2,3,4,7,12,12b-octahydroindolo[2,3-a]quinolizin-1-yl-propionic acid are added to a solution containing 2.04 g. (0.02 moles) of N-methylmorpholine (redistilled from sodium) in 20 ml. of dry tetrahydrofuran while stirring under nitrogen, then the solution is cooled to −5° C. and 1.10 g. (0.01 mole) of ethyl chloroformate are rapidly dropped in while stirring vigorously and keeping the inner temperature at or lower than 0° C. The mixture is stirred at 0° C. for 30 minutes, whereupon a solution containing 0.83 g. (0.11 moles) of N-methyl-2-hydroxyethylamine in 10 ml. of dry tetrahydrofuran is dropwise added at a temperature at or lower than 0° C. during 10 minutes. The mixture is stirred at 0° C. for 30 minutes and during an additional stirring for 4 hours the mixture is allowed to warm to room temperature. The mixture is evaporated on a rotating evaporator. After shaking thoroughly the residue with 50 ml. of dichloromethane and 20 ml. of water, the insoluble precipitate is filtered out and the organic phase is separated. The dichloromethane solution is washed four times with 20 ml of water each, dried over anhydrous magnesium sulphate and evaporated. The obtained residue which is the crude product, is purified by column chromatography on silica gel by using toluene containing 10% of diethylamine as eluant to give 0.43 g. (11.2% yield) of the title compound as a light yellow oil.

$^1$H-NMR spectrum (CDCl$_3$): δ 0.65 (3H, t, J=7 Hz, Cl—CH$_3$—C$\underline{H}_3$), 3.08 (3H, broad s, N—CH$_3$), 3.37 (1H, broad s, C12b—H), 3.60 (2H, broad t, N—CH$_2$), 3.78 (2H, t, C$\underline{H}_2$—OH), 6.9-7.5 (4H, m, aromatic protons), 9.9+10.1 (1H, broad s, indole NH) ppm.

Example 40

Preparation of
(+)-trans-1-ethyl-1,2,3,4,6,7,12,12b-octahydroindolo[2,3-a]quinolizin-1-yl-propionic acid 2-pyridylmethylamide The process described in Example 39 is followed, except that 1.19 g. (0.011 moles) of 2-pyridylmethylamine are used as amine component. The crude product is purified by column chromatography on silica gel by using toluene containing 10% of diethylamine as eluant to give 0.26 g. (6.2% yield) of the title compound as a sirupy product.

$^1$H-NMR spectrum (CDCl$_3$): δ0.65 (2H, J=7.5 Hz, Cl—CH$_2$—C$\underline{H}_3$), 3.40 (1H, broad s, C12b—H), 4.64 (2H, d, J$_{CH2,NH}$=5 Hz, NH—C$\underline{H}_2$), 7.0 (1H, CO—NH), 6.9-8.5 (6H, m, aromatic protons+C3'—H+C5°—H), 7.65 (1H, m, C4'—H), 8.54 (1H, m, C60'—H), 10.14 (1H, broad s, indole NH) ppm.

Example 41

Preparation of
(+)-trans-1-ethyl-1,2,3,4,6,7,12,12b-octahydroindolo[2,3-a]quinolizin-1-yl-propionic acid furfurylamide The process described in Example 39 is followed, except that 1.07 g. (0.011 moles) of furfurylamine are used as amine component. The crude product is purified by column chromatography on silica gel by using toluene containing 10% of diethylamine as eluant to give 0.47 g. (11.6% yield) of the title compound as a sirupy product.

$^1$H-NMR spectrum (CDCl$_3$): δ 0.64 (3H, t, J=7 Hz, Cl—CH$_2$—C$\underline{H}_3$), 3.37 (1H, broad s, C12B—H), 4.50 (2H, d, J$_{CH2NH}$=5.2 Hz, NH—C$\underline{H}_2$), 5.90 (1H, broad t, CO—NH), 6.25 (1H, dd, J=3.4+0.8 Hz, C3'—H), 6.33 (1H, dd, J=3.4+2.0 Hz, C4'—H), 6.9-7.5 (5H, m, aromatic protons+C5'—H), 10.02 (broad s, indole NH) ppm.

Example 42

Preparation of
(+)-trans-1-ethyl-1,2,3,4,6,7,12,12b-octahydroindolo[2,3-a]quinolizin-1-yl-propionic acid (S)-1-phenylethylamide 3.26 g. (0.01 mole) of (+)-trans-1-ethyl-1,2,3,4,6,7,12,12b-octahydroindolo[2,3-a]quinolizin-1-yl-propionic acid are added to a solution containing 2.04 g. (0.02 moles) of N-methylmorpholine (redistilled from sodium) in 20 ml of dry tetrahydrofuran while stirring under nitrogen, then the solution is cooled to −15° C. and 1.37 g. (0.01 mole) of isobutyl chloroformate are rapidly added dropwise while stirring vigorously and keeping the inner temperature at or lower than −15° C. The mixture is stirred at −15° C. for 30 minutes, whereupon a solution containing 1.33 g. (0.011 moles) of (S)-1-phenylethylamine in 10 ml. of dry tetrahydrofuran is dropwise added at a temperature at or lower than −15° C. during 10 minutes. The mixture is stirred at −15° C. for 30 minutes, and during an additional stirring for 4 hours the mixture is allowed to warm to room temperature. Then the mixture is evaporated on a rotating evaporator. After shaking thoroughly the residue with 50 ml. of dichloromethane and 20 ml. of water, the insoluble precipitate is filtered out and the organic phase is separated. The dichloromethane solution is washed four times with 20 ml. of water each, dried over anhydrous magnesium sulphate and evaporated. The residue which is the crude title product, is recrystallized from isopropanol to give 0.64 g. (14.8% yield) of the title compound, m.p.: 90°-92° C., [α]$_D^{25}$=−98.4° (c=1.0, chloroform).

$^1$H-NMR spectrum (CDCl$_3$): δ0.62+0.65 (3H, t, J=7.6 Hz, Cl—CH$_2$—C$\underline{H}_3$), 1.49+1.52 (3H, d, J=7 Hz, NH—CH—C$\underline{H}_3$), 3.36 (1H, broad s, C12b—H), 5.22 (1H, qd, J$_{CH,NH}$=7 Hz, NH—C$\underline{H}$), 5.86 (1H, broad d, CO—NH), 6.9-7.5 (9H, m, aromatic protons), 10.1 (1H, broad s, indole NH) ppm.

Example 43

Preparation of
(+)-trans-1-ethyl-1,2,3,4,6,7,12,12b-octahydroindolo[2.3-a]quinolizin-1-yl-propionic acid (R)-1-phenylethylamide The process described in Example 42 followed, except that 1.33 g. (0.011 moles) of (R)-1-phenylethylamine are used as amine component. The crude product is purified by recrystallization from isopropanol to give 0.7 g. (16.3% yield) of the title compound, m.p.: 90°–92° C., $[\alpha]_D^{25} = -100°$ (c=1.0, chloroform).

$^1$H-NMR spectrum (CDCl$_3$): δ0.62+0.65 (3H, t, J=7.5 Hz, Cl—CH$_2$CH$_3$), 1.50+1.53 (3H, d, J=7 Hz, NH—CH—CH$_3$), 3.36 (1H, broad s, C12b—H), 5.22 (1H, qd, J$_{CH,NH}$=7 Hz, NH—CH), 5.81 (1H, broad d, CO—NH), 6.9–7.5 (9H, m, aromatic protons), 10.06 (1H, broad s, indole NH) ppm.

Example 44

Preparation of
(+)-trans-1-ethyl-1,2,3,4,6,7,12,12b-octahydroindolo[2,3-a]quinolizin-1-yl-propionic acid (R)-1-phenylethylamide A mixture containing 1.70 g. (0.005 moles) of (+)-trans-1-ethyl-1,2,3,4,6,7,12,12b-octahydroindolo[2,3-a]quinolizin-1yl-propionic acid methyl ester, 0.63 g. [0.0052 moles] of (R)-1-phenylethylamine and 0.324 g. (0.006 moles) of sodium methoxide powder in 15 ml. of dry toluene is boiled under argon while stirring at such a rate that the methanol formed is distilled out together with toluene. After boiling for 6.5 hours the reaction mixture is decomposed by adding water, the toluene phase is dried over anhydrous magnesium sulphate and evaporated. The residue, which is the crude product, is purified by column chromatography on silica gel by using cyclohexane containing 10% of diethylamine as eluant to give 0.70 g. (32.6% yield) of the title compound.

Example 45

Preparation of
(−)-(1S,12bS)-1-ethyl-1,2,3,4,6,7,12,12b-octahydroindolo[2,3-a]quinolizin-1-yl-propionic acid diethylamide The process described in Example 1 is followed, except that 1.46 g. (0.02 moles) of diethylamine are used as amine component. The crude product is purified by recrystallization from toluene to give 2.33 g. (61% yield) of the title compound, m.p. 222°–227° C., $[\alpha]_D^{25} = -124.2°$ (c=1.5, chloroform).

Analysis: calculated for C$_{24}$H$_{35}$N$_3$O (molecular weight 381.54): C 75.54; H 9.25; N 11.01%. found: C 75.81; H 9.01; N 11.10%.

$^1$H-NMR spectrum (CDCl$_3$): δ 1.09 (3H, t, J=7 Hz, Cl—CH$_2$—CH$_3$), 0.73 and 0.99 (6H, t, J=7 Hz, N—CH$_2$—CH$_3$), 2.9–3.3 (4H, m, N—CH$_2$—CH$_3$), 3.34 (1H, C12b—H), 7.0–7.48 (4H, m, aromatic protons), 8.1 (1H, broad s, indole NH) ppm.

The *ethanesulphonate salt* metls at 205°–207° C. (after recrystallization from isopropanol), $[\alpha]_D^{25} = -79.3°$ (c=2.0, water).

Analysis: calculated for C$_{24}$H$_{35}$N$_3$O$_4$S (molecular weight 491.67): C 63.51; H 8.41; N 8.55; S 6.52%. found: C 63.49; H 8.25; N 8.55; S 6.63%.

Example 46

Preparation of
(−)-(1S,12bS)-1-ethyl-1,2,3,4,6,7,12,12b-octahydroindolo[2,3-a]quinolizin-1-yl-propionic acid N-methylpiperazide The process described in Example 1 is followed, except that 2.00 g. (0.02 moles) of N-methylpiperazine are used as amine component. The crude product is purified by column chromatography on silica gel by using toluene containing 5% of diethylamine as eluant to give 2.77 g. (68% yield) of the title compound as a foamy product, $[\alpha]_D^{25} = -127.2°$ (c=2.0, chloroform).

$^1$H-NMR spectrum (CDCl$_3$): δ 1.10 (3H, t, J=7 Hz, Cl—CH$_2$—CH$_3$), 2.14 (3H, s, N—CH$_3$), 3.32 (1H, C12b—H), 7.0–7.48 (4H, m, aromatic protons), 7.48 (1H, broad s, indole NH) ppm.

The *bis-hydrobromide salt* melts at 225°–240° (after recrystallization from isopropanol), $[\alpha]_D^{23} = -73.1°$ (c=2.0, water).

Analysis: calculated for C$_{25}$H$_{38}$Br$_2$N$_4$O (molecular weight 570.40): C 52.64; H 6.72; N 9.82; Br (ionic) 28.02%. found: C 53.09; H 7.01; N 9.56; Br (ionic) 27.82%.

Example 47

Preparation of
(−)-(1s,12bS)-1-ethyl-1,2,3,4,6,7,12,12b-octahydroindolo[2,3-a]quinolizin-1-yl-propionic acid (R)-1-phenylethylamide A mixture containing 1.63 g. (0.05 moles) of (−)-(1S,12bS)-1-ethyl-1,2,3,4,6,7,12,12b-octahydroindolo[2,3a]quinolizin-lyl-propionic acid and 0.67 g. (0.0055 moles) of (R)-1-phenylethylamine in 30 ml. of dry xylene is slowly boiled under nitrogen while stirring and slowly distilling out the xylene. The evaporated xylene is occasionally substituted by adding dry xylene. After boiling for 9 hours the mixture is evaporated under reduced pressure and the residue is extracted twice with 25 ml. of dichloromethane each, then the dichlormethane solution is evaporated. The crude residue is purified by column chromatography on silica gel by using toluene containing 5% of diethylamine as eluant. The obtained product is recrystallized from isopropanol to give 0.205 g. (9.6% yield) of the title product, m.p.: 152°–155° C.

Example 48

Preparation of
(−)-(1S,12bS)-1-ethyl-12-methyl-1,2,3,4,6,7,12,12b-octahydroindolo[2,3a]quinolizin-1-yl-propionic acid methyl ester 0.005 g. of ferric nitrate nonahydrate and then in little portions 0.25 g. of sodium are added to 20-25 ml. of liquid ammonia at −70° C. under vigorous stirring. After dissolution of the sodium, disappearing of the blue colour and after precipitation of sodium amide as a grey solid, the reaction mixture is allowed to warm to a temperature between −50° C. and −55° and then 3.4 g. (0.01 mole) of (−)-(1S,12bS)-1-ethyl-1,2,3,4,6,7,12,12b-octahydroindolo[2,3-a]quinolizin-1-yl-propionic acid methyl ester dissolved in 20 ml of anhydrous ether are added and stirred at −50° C. for 10 minutes. Thereupon a solution of 1.56 g. (0.011 moles) of methyl iodide in 5 ml. of anhydrous ether is portionwise added and the mixture is allowed to warm to room temperature. After evaporation of the ammonia, an oily crude product is obtained by extraction with ether. This crude product is purified by column chromatography on 200 g. of Kieselgel 60 (0.063-0.2 mm.) by using toluene containing 10% of diethylamine as eluant to give 2.1 g. (59.3% yield) of the title product as a light yellow oil with an $R_f$ value of 0.78 (Polygram SIL G/UV$_{254}$; developed by toluene containing 10% of diethylamine; detected by UV light).

Example 49

Preparation of (−)-(1S,12bS)-1-ethyl-12-methyl-1,2,3,4,6,7,12,12b-octahydroindolo[2,3-a]quinolizin-1yl-propionic acid The solution of 10.0 g. (0.028 moles) of (−)-(1S,12bS)-1-ethyl-12-methyl-1,2,3,4,6,7,12,12b-octahydroindolo[2,3-a]quinolizin-1-yl-propionic acid methyl ester (prepared as described in Example 48) in 200 ml. of 96% of ethanol containing 2.5 g. (0.044 moles) of potassium hydroxide is refluxed for one hour. After cooling down, the solution is evaporated to dryness, the evaporation residue is dissolved in a little amount of water and acidified to pH 6 by adding acetic acid. The precipitated product is filtered, washed with water and dried to give 6.28 g. (66.0% yield) of the title compound with an $R_f$ value of 0.51 (Polygram SIL G/UV$_{254}$; developed by an 5:1 mixture of isopropanol with 25% aqueous ammonia solution; detected by UV light).

The *hydrochloride salt* decomposes from 180° C. (after recrystallizatio from ethanol), $[\alpha]_D^{25} = -71.5°$ (c=1.0, water).

Analysis: calculated for $C_{21}H_{29}ClN_2O_2$ (molecular weight 376.9); C 66.91; H 7.75; N 7.43; Cl (ionic) 9.41%. found: C 67.11; H 7.81; N 7.49; Cl (ionic) 9.41%.

Example 50

Preparation of (−)-(1S,12bS)-1-ethyl-12-methyl-1,2,3,4,6,7,12,12b-octahydroindolo[2,3-a]quinolizin-1-yl-propionic acid benzylamide 3.40 g. (0.01 moles) of (−)-(1S,12bS)-1-ethyl-12-methyl-1,2,3,4,6,7,12,12b-octahydroindolo[2,3-a]quinolizin-1-yl-propionic acid are added to a solution containing 2.04 g. (0.02 moles) of N-methylmorpholine (redistilled from sodium) in 20 ml. of dry tetrahydrofuran while stirring under nitrogen, then the solution is cooled to −5° C. and 1.10 g. (0.01 mole) of ethyl chloroformate are rapidly dropped in while stirring vigorously and keeping the inner temperature at or lower than 0° C. The mixture is stirred at 0° C. for 30 minutes, whereupon a solution containing 1.18 g. (0.011 moles) of benzylamine in 10 ml. of dry tetrahydrofuran is dropwise added at a temperature between −5° C. and 0° C. during 10 minutes. The mixture is stirred at 0° C. for 30 minutes, then during an additional stirring for 4 hours the mixture is allowed to warm to room temperature. The mixture is evaporated on a rotating evaporator and after shaking thoroughly the residue with 50 ml. of dichloromethane and 20 ml. of water, the phases are separated. The dichloromethane layer is washed at first with 20 ml. of 5% sodium carbonate solution, then three times with 20 ml. of water each, dried over anhydrous magnesium sulphate and evaporated. The residue which is the crude product, is purified by column chromatography on silica gel by using toluene containing 10% of diethylamine to give 3.36 g. (78% yield) of the title compound as an oily product.

$^1$H-NMR spectrum (CDCl$_3$): δ0.91 (3H, t, J=7 Hz, Cl—CH$_2$CH$_3$), 3.42 (1H, s, C12b—H), 3.53 (3H, s, indole NCH$_3$), 3.85+4.35 (2H, broad, NH—CH$_2$), 6.9 (1H, broad, CO—NH), 6.9-7.4 (9H, m, aromatic protons) ppm.

The D-tartrate salt melts at 167°-170° C. (after recrystallization from the mixture of ethanol and acetone).

Analysis: calculated for $C_{32}H_{41}N_3O_7$ (molecular weight 579.67): C 66.30; H 7.13; N 7.25%. found: C 66.27; H 7.29; N 7.18%.

Example 51

Preparation of (−)-(1S,12bS)-1-ethyl-12-methyl-1,2,3,4,6,7,12,12b-octahydroindolo[2,3-a]quinolizin-1-yl-propionic acid N-methyl-2-hydroxyethylamide The process described in Example 48 is followed, except that 0.83 g. (0.011 moles) of N-methyl-2-hydroxyethylamine is used as amine component. The crude product is purified by column chromatography on silica gel by using toluene containing 10% of diethylamine as eluant to give 2.31 g. (58% yield) of the title compound as a sirupy product.

$^1$H-NMR spectrum (CDCl$_3$): δ0.92 (3H, t, J;32 7 Hz, Cl—CH$_2$CH$_3$), 2.74 (3H, broad s, N—CH$_3$), 3.32 (2H, broad s, N—CH$_3$), 3.32 (2H, broad t, N—CH$_2$), 3.43 (1H, s, C12b—H), 3.58 (2H, t, CH$_2$—OH), 3.58 (3H, s, indole N—CH$_3$), 6.95-7.55 (4H, m, aromatic protons) ppm.

$^{13}$C-NMR spectrum (CDCl$_3$): δ 7.96 (Cl—CH$_2$CH$_3$9, 21.56++21.49 (C3), 23.21 (C7), 26,80+26.58 (C14), 27.16 (C13), 30.18 (Cl—CH$_2$CH$_3$) 34.21+33.85 (indole NCH$_3$), 35.93+34.34 (CO—NCH$_3$), 37.85 (C2), 42.65 (C1), 51.34 (C6), 51.47+51.17 (N—CH$_2$CH$_2$—OH), 56.60 (C4), 61.44+59.72 (—CH$_2$OH), 65.90 (C12b), 109.98+110,24 (C11), 113.79++113.57 (C7a), 117.74++117.67 (C8), 119.52 (C9), 121.49 (C10), 127.63 (C7b), 137.84 (C12a), 140.55 (C11a), 175.80++174.16 (NCO).

Example 52

Preparation of (+)-1α,2,3,4,6,7,12,12bα-octahydroindolo[2,3-a]quinolizin-1-yl-propionic acid (R)-1-phenylethylamide 1.33 g. (0.011 moles) of (R)-1-phenylethylamine are acylated with 3.12 g. (0.01 mole) of (+)-1α,2,3,4,6,7,12,12bα-octahydroindolo[2,3-a]quinolizin-1-yl-propionic acid as described in Example 1 to give 1.6 g. (36.3% yield) of the title compound as a foamy product with an $R_f$ value of 0.44 (Polygram SIL G/UV$_{254}$; developed by ethyl acetate containing 5% of triethylamine; detected by UV light).

Example 53

Preparation of (−)-(1S,12bS)-1-ethyl-8-nitro-1,2,3,4,6,7,12,12b-octahydroindolo[2,3-a]quinolizin-1-yl-propionic acid methyl ester and (−)-(1s,12bS)-1-ethyl-10-nitro-1,2,3,4,6,7,12,12b-octahydroindolo[2,3-a]quinolizin-1-yl-propionic acid methyl ester A solution containing 4.8 g. (0.014 moles) of (−)-(−)-(1S,12bS)-1-ethyl-1,2,3,4,6,7,12,12B-octahydroindolo[2,3-a]quinolizin-1-yl-propionic acid methyl ester in 25 ml. of anhydrous acetic acid is dropped to the mixture of 7.5 ml. of anhydrous acetic acid and 7.5 ml. of 100% nitric acid (d=1.52) cooled to a temperature between 0° C. and −0° C. while vigorous stirring. After the addition the mixture is stirred for 5 minutes and then poured into 250 ml. of ice-water. The mixture is neutralized by adding concentrated ammonia solution, extracted with chloroform and the organic phase is dried over anhydrous magnesium sulphate. After evaporation, the crude residue is purified by column chromatography on 500 g. of Kieselgel 60 (0.063–0.2 mm.) by using toluene containing 10% of diethylamine as eluant in order to separate to following components:

(−)-(1S,12bS)-1-ethyl-8-nitro-1,2,3,4,6,7,12,12b-octahydroindolo[2,3-a]quinolizin-1-yl-propionic acid methyl ester is obtained in a yield of 1.15 g (21%), m.p. 133°–136° C. (after recrystallization from a mixture of toluene and diisopropyl ether) with an $R_f$ value of 0.43 (Polygram SIL G/UV$_{254}$; developed by toluene containing 10% of diethylamine; detected by UV light).

(−)-(1S,12bS)-1-ethyl-10-nitro-1,2,3,4,6,7,12,12b-octahydroindolo[2,3-a]quinolizin-1-yl-propionic acid methyl ester is obtained in a yield of 1.95 g. (36%), m.p.: 177°–180° C. (after recrystallization from methanol) with an $R_f$ value of 0.60 (Polygram SIL G/UV$_{254}$; developed by toluene containing 10% of diethylamine; detected by UV light).

Example 54

Preparation of
(−)-(1S,12bS)-1-ethyl-10-nitro-1,2,3,4,6,7,12,12b-octahydroindolo[2,3-a]quinolizin-1-yl-propionic acid A solution containing 0.385 g (0.001 mole) of (−)-(1S,12bS)-1d-ethyl-10-nitro-1,2,3,4,6,7,12,12b-octahydroindolo[2,3-a]quinolizin-1-yl-propionic acid methyl ester (prepared as described in Example 53) dissolved in the mixture of 0.169 g. (0.003 moles) of potassium hydroxide in 8 moles of 96% ethanol is refluxed for 20 minutes, then evaporated. The residue is dissolved in a little amount of water and acidified to pH 6 by adding acetic acid. The precipitate is filtered, washed with water and dried to give 0.300 g. (81% yield) of the title compound which can be used without purification for the preparation of the acid amide.

Example 55

Preparation of
(−)-(1S,12bS)-1-ethyl-10-nitro-1,2,3,4,6,7,12,12b-octahydroindolo[2,3-a]quinolizin-1-yl-propionic acid (R)-1-phenylethylamide 0.371 g. (0.001 mole) of (−)-()1S,12bS)-1-ethyl-10-nitro-1,2,3,4,6,7,12,12b-octahydroindolo[2,3-a]quinolizin-1-yl-propionic acid is added to a solution containing 0.111 g. (0.0011 moles) of N-methylmorpholine (redistilled from sodium) in 4 ml. of dry tetrahydrofuran while stirring under nitrogen, then the solution is cooled to 0° C. and 0.108 g. (0.001 mole) of ethyl chloroformate is rapidly added dropwise while stirring vigorously and keeping the inner temperature at or lower than 0° C. for 30 minutes, whereupon a solution containing 0.133 g. (0.0011 moles) of (R)-1-phenylethylamine in 1 ml. of dry tetrahydrofuran is dropwise added at 0° C. while stirring, finally the mixture is stirred at 0° C. for 30 minutes at room temperature for additional 4 hours. Thereupon the reaction mixture is evaporated on a rotating evaporator and after shaking thoroughly the residue with 10 ml. of dichloromethane and 5 ml. of water, the phases are separated. The dichloromethane solution is washed at first with 5 ml of 5% sodium carbonate solution, then three times with 5 ml of water each, dried over anhydrous magnesium sulphate and evaporated. The crude residue is purified by column chromatography on silica gel by using toluene containing 10% of diethylamine as eluant to give 0.33 g (69.6% yield) of the title compound, M.P.: 130°–132° C., $[\alpha]_D^{23} = -140.5$ (C=1.0 chloroform) with and $R_f$ value of 0.43 (polygram sil G/UV 254: developed by toluene containing 10% of diethylamine: detected by UV light).

Example 56

Preparation of
(−)-(1S,12bs)-1-ethyl-8-nitro-1,2,3,4,6,7,12,12b-octahydroindolo[2,3-a]quinolizin-1-yl-propionic acid The process described in Example 54 is followed by using 0.385 g (0.001 mole) of (−)-(1S,12bs)-1-ethyl-8-nitro-1,2,3,4,6,7,12,12b-octahydroindolo[2,3-a]quinolizin-1-yl-propionic acid methyl ester (prepared as described in Example 53) as starting material to give 0.289 g (78% yield) of the title compound which can be used without purification for the preparation of acid amides.

Example 57

Preparation of
(−)-(1S,12bs)-1-ethyl-8-nitro-1,2,3,4,6,12,12b-octahydro[2,3-a]quinolizin-1-yl-propionic acid (R)-1-phenylethylamide The process described in Example 55 is followed, except that the acylation is carried out with 0.371 g (0.001 mole) of (−)-(1S,12bS)-1-ethyl-8-nitro-1,2,3,4,6,7,12,12b-octahydroindolo[2,3-a]quinolizin-1-yl-propionic acid (prepared as described in Example 56) to give 0.27 g. (57% yield) of the title compound, m.p.: 220°–222° C., $[\alpha]_D^{23} 2 - 232.3°$ (c=1.0, chloroform) with an $R_f$ value of 0.27 (Polygram SIL G/UV$_{254}$; developed by toluene containing 10% of diethylamine; detected by UV light).

Example 58

Preparation of
(−)-(1S,12bS)-9-bromo-1-ethyl-1,2,3,4,6,7,12,12b-octahydroindolo[2,3-a]quinolizin-1-yl-propionic acid methyl ester and (−)-(1S,12bS)-8,9-dibromo-1-ethyl-1,2,3,4,6,7,12,12b-octahydroindolo[2,3-a]quinolizin-1-yl-propionic acid methyl ester 0.59 g. (0.0033 moles) of freshly recrystallized N-bromosuccinimide is added to the solution of 1.02 g. (0.003 moles) of (−)-(1S,12bS)-1-ethyl-1,2,3,4,6,7,12,12b-octahydroindolo[2,3-a]quinolizin-1-yl-propionic acid methyl ester in 10 ml. of trifluoroacetic acid and the mixture is set aside at room temperature overnight. Then the solution is made alkaline by adding 20% aqueous sodium carbonate solution, extracted with chloroform, the chloroformic phase is dried over anhydrous magnesium sulphate and evaporated on a rotating evaporator. The evaporation residue which is the crude product, is purified by column chromatography on 150 g. of Kieselgel 60 (0.063–0.2 mm.) by using cyclohexane containing 10% of diethylamine as eluant in order to separate the following components:

(−)-(1S,12bS)-9-bromo-1-ethyl-1,2,3,4,6,7,12,12b-octahydroindolo[2,3-a]quinolizin-1-yl-propionic acid methyl ester is obtained in a yield of 0.34 g. (27%) as a foamy product with an $R_f$ value of 0.26 (Polygram SIL G/UV$_{254}$; developed by cyclohexane containing 10% of diethylamine; detected by UV light).

(−)-(1S,12bS)-8,9-dibromo-1-ethyl-1,2,3,4,6,7,12,12b-octahydroindolo[2,3-a]quinolizin-1-yl-propionic acid methyl ester is obtained in a yield of 0.12 g. (8%) as a foamy product with an $R_f$ value of 0.16 (Polygram SIL G/IV$_{254}$; developed by cyclohexane containing 10% of diethylamine; detected by UV light).

Example 59

Preparation of
(−)-(1S,12bS)-9-bromo-1-ethyl-1,2,3,4,6,7,12,12b-octahydroindolo[2,3-a]quinolizin-1-yl-propionic acid The process described in Example 54 is followed by using 0.419 g. (0.001 mole) of (−)-(1S,12bS)-9-bromo-1-ethyl-1,2,3,4,6,7,12,12b-octahydroindolo[2,3-a]quinolizin-1-yl-propionic acid methyl ester (prepared as described in Example 58) to give 0.313 g. (77% yield) of the title compound which can be used without purification for the preparation of acid amides.

Example 60

Preparation of
(−)-(1S,12bS)-9-bromo-1-ethyl-1,2,3,4,6,7,12,12b-octahydroindolo[2,3-a]quinolizin-1-yl-propionic acid (R)-1-phenylethylamide The process described in Example 55 is followed, except that the acylation is carried out with 0.405 g. (0.001 mole) of (−)-(1S,12bS)-9-bromo-1-ethyl-1,2,3,4,6,7,12,12b-octahydroindolo[2,3-a]quinolizin-1-yl-propionic acid (prepared as described in Example 59) to give 0.2 g. (39% yield) of the title compound as a foamy product, $[\alpha]_D^{23} = -24.7°$ (c=1.0, chloroform) with an $R_f$ value of 0.43 (Polygram SIL G/UV$_{254}$; developed by toluene containing 10% of diethylamine; detected by UV light).

Example 61

Preparation of
(−)-(1S,12bS)-8,9-dibromo-1-ethyl-1,2,3,4,6,7,12,12b-octahydroindolo[2,3-a]quinolizin-1-yl-propionic acid The process described in Example 54 is followed by using 0.498 g. (0.001 mole) of (−)-(1S,12bS)-8,9-dibromo-1-ethyl-1,2,3,4,6,7,12,12b-octahydroindolo[2,3-a]quinolizin-1-yl-propionic acid methyl ster (prepared as described in Example 58) as starting material to give 0.368 g. (76% yield) of the title compound which can be used without purification for the preparation of acid amides.

Example 62

Preparation of
(+)-(1S,12bS)-8,9-dibromo-1-ethyl-1,2,3,4,6,7,12,12b-octahydroindolo[2,3-a]quinolizin-1-yl-propionic acid (R)-1-phenylethylamide The process described in Example 55 is followed except that the acylation is carried out with 0.484 g. (0.001 mole) of (−)-(1S,12bS)-8,9-dibromo-1-ethyl-1,2,3,4,6,7,12,12b-octahydroindolo[2,3-a]quinolizin-1-yl-propionic acid (prepared as described in Example 61) to give 0.24 g. (41% yield) of the title compound as a foamy product, $[\alpha]_D^{23} = +10.4°$ (c=0.5, chloroform) with an $R_f$ value of 0.36 (Polygram SIL G/UV$_{254}$; developed by toluene containing 10% of diethylamine; detected by UV light).

Example 63

Preparation of
(−)-(1S,12bS)-1-ethyl-1,2,3,4,6,7,12,12b-octahydroindolo[2,3-a]quinolizin-1-yl-propionic acid 4-fluorobenzylamide The process described in Example 1 is followed, except that 1.38 g. (0.011 moles) of 4-fluorobenzylamine are used as amine component. The crude product is purified by column chromatography on silica gel by using toluene containing 10% of diethylamine as eluant to give 2.93 g. (68% yield) of the title compound as an oil which becomes crystalline on standing, m.p.: 92°–96° C., $[\alpha]_D^{25} = -115.8°$ (c=2.0, chloroform). The $R_f$ value of this compound is 0.37 (Polygram SIL G/UV$_{254}$; developed by toluene containing 5% of diethylamine; detected by UV light).

Example 64

Preparation of
(−)-(1S,12bS)-1-ethyl-1,2,3,4,6,7,12,12b-octahydroindolo[2,3-a]quinolizin-1-yl-propionic acid 2-thienylmethylamide The process described in Example 1 is followed, except that 1.25 g. (0.011 mole) of 2-thienylmethylamine are used as amine component. The crude product is purified by column chromatography on silica gel by using toluene containing 5% of diethylamine as eluant to give 3.10 g. (74% yield) of the title compound as an oily product which becomes crystalline on standing, m.p.: 80°–85° C., $[\alpha]_D^{25} = -101.1°$ (c=2.0, chloroform). The $R_f$ value of this compound is 0.32 (Polygram SIL G/UV$_{254}$; developed by toluene containing 5% of diethylamine; detected by UV light).

Example 65

Preparation of
(−)-(1S,12bS)-1-ethyl-1,2,3,4,6,7,12,12b-octahydroindolo[2,3-a]quinolizin-1-yl-propionic acid piperidide The process described in Example 1 is followed, except that 0.94 g. (0.011 moles) of piperidine is used as amine component. The crude product is purified by column chromatography on silica gel by using toluene containing 5% of diethylamine as eluant to give 2.59 g. (65% yield) of the title compound as a foamy product, $[\alpha]_D^{25} = -125.5°$ (c=2.0, chloroform) with an $R_f$ value of 0.41 (Polygram SIL G/UV$_{254}$; developed by toluene containing 5% of diethylamine; detected by UV light).

Example 66

Preparation of
(−)-(1S,12bS)-1-ethyl-1,2,3,4,6,7,12,12b-octahydroindolo[2,3-a]quinolizin-1-yl-propionic acid morpholide The process described in Example 1 is followed, except that 0.96 g. (0.011 moles) of morpholine is used as a amine component. The crude product is purified by column chromatography on silica gel by using toluene containing 10% of diethylamine as eluant to give 2.83 g. (71% yield) of the title compound as a foamy product, $[\alpha]_D^{25} = -119.9°$ (c=2.1, chloroform) with an $R_f$ value of 0.38 (Polygram SIL G/UV$_{254}$; developed by toluene containing 5% of diethylamine; detected by UV light).

Example 67

Preparation of
(−)-(1S,12bS)-1-ethyl-1,2,3,4,6,7,12,12b-octahydroindolo[2,3-a]quinolizin-1-yl-propionic acid cyclohexylamide The process described in Example 1 is followed, except that 1.08 g. (0.011 moles) of cyclohexylamine are used as amine component. The crude product is purified by column chromatography by using toluene containing 10% of diethylamine as eluant to give 3.05 g. (74% yield) of the title compound as a foamy product, $[\alpha]_D^{25} = -106.9°$ (c=2.0, chloroform) with an $R_f$ value of 0.46 (Polygram SIL G/UV$_{254}$; developed by toluene containing 5% of diethylamine; detected by UV light).

Example 68

Preparation of
(−)-(1S,12bS)-1-ethyl-1,2,3,4,6,7,12,12b-octahydroindolo[2,3-a]quinolizin-1-yl-propionic acid 1-naphthylmethylamide The process described in Example 1 is followed, except that 1.73 g. (0.011 moles) of 1-naphthlmethylamine are used as amine component. The crude product is purified by column chromatography by using toluene containing 10% of diethylamine as eluant to give 3.41 g. (72% yield) of the title compound as a foamy product, $[\alpha]_D^{25} = -95.8°$ (c=2.1. chloroform) with an $R_f$ value of 0.35 (Polygram SIL G/UV$_{254}$; developed by toluene containing 5% of diethylamine; detected by UV light).

Example 69

Preparation of
(−)-(1S,12bS)-1-ethyl-1,2,3,4,6,7,12,12b-octahydroindolo[2,3-a]quinolizin-1-yl-propionic acid 4-pyridylamide The process described in Example 1 is followed, except that 1.04 g. (0.011 moles) of 4-aminopyridine are used as amine component. The crude product is purified by column chromatography by using toluene containing 30% of diethylamine as eluant to give 1.14 g. (28% yield) of the title compound as a foamy product, $[\alpha]_D^{25} = -163.5°$ (c=2.0, chloroform) with an $R_f$ value of 0.42 (Polygram SIL G/UV$_{254}$; developed by toluene containing 30% of diethylamine; detected by UV light).

Example 70

Preparation of
(−)-(1S,12bS)-1-ethyl-1,2,3,4,6,7,12,12b-octahydroindolo[2,3-a]quinolizin-1-yl-propionic acid 5-hexenylamide The process described in Example 1 is followed, except that 1.08 g. (0.011 moles) of 5-hexenylamine are used as amine component. The crude product is purified by column chromatography by using carbon tetrachloride containing 10% of diethylamine as eluant to give 1.71 g. (42% yield) of the title compound as a very viscous oil, $[\alpha]_D^{24} = -101.4°$ (c=2.0, chloroform) with an $R_f$ value of 0.40 (Polygram SIL G/UV$_{254}$; developed by carbon tetrachloride containing 10% of diethylamine; detected by UV light).

Example 71

Preparation of
(+)-1α-ethyl-9-methoxy-1,2,3,4,6,7,12,12bα-octahydroindolo[2,3-a]quinolizin-1β-yl-propionic acid benzylamide The process described in Example 1 is followed by acylating 0.024 g. (0.00022 moles) of benzylamine with 0.071 g. (0.0002 moles) of (+)-1α-ethyl-9-methoxy-1,2,3,4,6,7,12,12bα-octahydroindolo[2,3-a]quinolizin-1β-yl-propionic acid. The crude product is purified by column chromatography by using toluene containing 10% of diethylamine as eluant to give 0.023 g. (26% yield) of the title compound as a foamy product, with an $R_f$ value of 0.39 (Polygram SIL G/UV$_{254}$; developed by toluene containing 10% of diethylamine; detected by UV light).

We claim:

1. A compound of the Formula (I)

wherein
$R_1$ and $R_2$ stand independently for a hydrogen or halogen atom, or a hydroxyl, nitro or $C_1$ to $C_4$ alkoxy group;
$R_3$ and $R_4$ stand independently for a hydrogen atom or a $C_1$ to $C_4$ alkyl group; and
$R_5$ and $R_6$ are each independently selected from the group consisting of $C_1$ to $C_8$ alkyl, $C_1$ to $C_8$ alkyl substituted by hydroxy or $C_1$ to $C_4$ alkoxy, $C_3$ to $C_8$ alkenyl, $C_3$ to $C_8$ cycloalkyl, phenyl, phenyl substituted by halo, acetyl, $C_1$ to $C_4$ alkyl, $C_1$ to $C_4$ alkoxy, phenyl or hydroxy, pyridyl, furyl, thienyl, pyrrolyl, imidazolyl, pyrimidinyl, thiezolyl, naphthyl, quinolinyl, indolyl, quinazolinyl, benzyl, benzyl substituted by one or two $C_1$ to $C_4$ alkyl, $C_1$ to $C_4$ alkoxy, halo or hydroxy, 1-phenyl-ethyl, 2-phenyl-ethyl, 4-phenyl-butyl, 1-naphthyl-methyl, furfuryl, 2-pyridyl-methyl, thiphen-2-yl-methyl, and 2-(3-indolyl)-ethyl; or
$R_5$ and $R_6$ together with the adjacent nitrogen to which they are attached form a $C_2$ to $C_8$ α'ω-alkylene group; or
$R_5$ and $R_6$ together with the adjacent nitrogen atom to which they are attached form a morpholinyl or N-methyl-piperazinyl group; and
G is a $C_1$ to $C_4$ straight alkylene chain; or a pharmaceutically acceptable acid addition salt thereof.

2. (−)-(1S,12bS)-1-ethyl-1,2,3,4,6,7,12,12b-octahydroindolo[2,3-a]quinolizin-1-yl-propionic acid (R)-1-phenylethylamide and the therapeutically useful acid addition salts thereof.

3. An anti-ulcer pharmaceutical composition which comprises as active ingredient the compound of the Formula (I) as defined in claim 1, or a pharmaceutically acceptable acid addition salt thereof, in admixture with a pharmaceutically acceptable inert carrier.

4. A method of treating a mammalian subject suffering from a condition which can be treated by a gastrocytoprotective agent which comprises the step of administering to said mammalian subject a therapeutically effective amount of a compound of the Formula (I) as defined in claim 1, or a pharmaceutically acceptable acid addition salt thereof.

* * * * *